(12) United States Patent
Tyeryar et al.

(10) Patent No.: US 7,763,603 B2
(45) Date of Patent: Jul. 27, 2010

(54) MANIPULATION OF BRAIN CDP-DIACYLGLYCEROL AND USES THEREOF

(76) Inventors: Kimberly R. Tyeryar, 371 A Vickers Rd., Chapel Hill, NC (US) 27517; Ashiwel S. Undie, 7829 Brookstone Ct., Ellicott City, MD (US) 21043

( * ) Notice: Subject to any disclaimer, the term of this patent is extended or adjusted under 35 U.S.C. 154(b) by 84 days.

(21) Appl. No.: 11/891,210

(22) Filed: Aug. 9, 2007

(65) Prior Publication Data

US 2008/0039443 A1 Feb. 14, 2008

Related U.S. Application Data

(60) Provisional application No. 60/836,904, filed on Aug. 10, 2006.

(51) Int. Cl.
| | |
|---|---|
| *C12Q 1/00* | (2006.01) |
| *A61K 31/135* | (2006.01) |
| *A61K 31/445* | (2006.01) |
| *A61K 31/47* | (2006.01) |
| *A61K 31/55* | (2006.01) |
| *A61K 47/00* | (2006.01) |
| *A61P 25/00* | (2006.01) |

(52) U.S. Cl. ............. 514/217; 514/310; 514/321; 514/651; 514/654; 514/789; 435/4

(58) Field of Classification Search ........... 514/217, 514/310, 321, 651, 654, 789; 435/4
See application file for complete search history.

(56) References Cited

U.S. PATENT DOCUMENTS

| | | | | |
|---|---|---|---|---|
| 4,310,524 | A | * | 1/1982 | Wiech et al. ............ 514/217 |
| 5,817,665 | A | * | 10/1998 | Dante ..................... 514/282 |
| 6,211,171 | B1 | * | 4/2001 | Sawynok et al. ...... 514/211.13 |

* cited by examiner

*Primary Examiner*—Sreeni Padmanabhan
*Assistant Examiner*—Sahar Javanmard
(74) *Attorney, Agent, or Firm*—Benjamin Aaron Adler

(57) ABSTRACT

Provided herein methods of screening for potential antidepressant compounds effective to increase production of cellular CDP-diacylglycerol and synthesis of inositol phospholipid in depression-related areas of the brain. Also, provided are methods of diagnosing and treating depressive or mood disorders in a subject by administering these screened antidepressant compounds. Further provided is a method of determining the therapeutic efficacy of an antidepressant drug regimen by comparing the ratio of CDP-diacylglycerol/inositol phosphate after treatment to a basal ratio in a subject.

8 Claims, 17 Drawing Sheets

MANIPULATION OF BRAIN CDP-DIACYLGLYCEROL AND USES THEREOF

CROSS-REFERENCE TO RELATED APPLICATION

This nonprovisional application claims benefit of priority of provisional U.S. Ser. No. 60/836,904, filed Aug. 10, 2006, now abandoned.

FEDERAL FUNDING LEGEND

This invention was produced in part using funds obtained through the National Institutes of Health NIDA Grant No. DA017614. Consequently, the federal government has certain rights in this invention.

BACKGROUND OF THE INVENTION

1. Field of the Invention

The present invention relates generally to the fields of psychiatric medicine and pharmacology. More specifically, the present invention provides methods to treat depressive disorders by targeting specific molecules in the brain.

2. Description of the Related Art

Major depression is a serious mood disorder that annually afflicts millions of people worldwide (1-3). Despite years of research, the biological causes and pathological mechanisms of major depressive disorder are unclear. Further, while treatments are available for managing the disease symptoms, efforts to develop safer and more effective medications are hampered because the mechanism of action of antidepressants is not well understood (4-5).

It is well known, however, that antidepressants with differing chemical and clinical properties can increase the synaptic levels of the neurotransmitters, i.e., serotonin, norepinephrine, and/or dopamine, in discrete brain regions (6-7). The monoamine transmitters may then activate their cognate postsynaptic receptors and modulate the activities of downstream signaling cascades to possibly produce the antidepressive effect. It remains to be clarified, however, which among the numerous postsynaptic receptors and signaling components may be involved in the mode of action of antidepressants (5, 8-9).

Receptors for the monoamine neurotransmitters are coupled to diverse signaling pathways, including adenylyl cyclase, phospholipases, and MAP kinase pathways (10-13). Aspects of each of these signaling systems have been investigated as potential downstream targets of antidepressive mechanisms (8, 14-15). As examples, acute or chronic treatment with various antidepressant compounds can lead to changes in basal or drug-induced activities of brain adenylyl cyclase (16-19), phospholipase A2, CREB, inositol phosphates (IPs), phosphoinositide-specific phospholipase C (PLC), phosphatidylinositides, protein kinase C (PKC), extracellular signal regulated kinase, ion channels, neurotrophins, and neuropeptides. Antidepressants can also enhance neurogenesis, modulate neuronal excitability, and alter the gene expression of various signaling components including neurotransmitter transporters, receptors, transducers, and effectors (39-46). While these observations indicate that changes in postsynaptic signaling cascades may constitute an integral component in the mechanisms that underlie depression or its treatment with antidepressant medications, no signaling cascade has been identified that explains the functional and clinical data.

Notably, the depression or antidepressant-related phosphoinositide observations have been corroborated by clinical studies showing that depressed persons have reduced cortical levels of the phosphoinositide precursor myo-inositol (47-48). Moreover, oral ingestion of pharmacological doses of myo-inositol may elicit antidepressive responses in rodents and enhance the recovery of clinically depressed patients (49-51). Consistent with these findings, chronic administration of antidepressant agents has been associated with increased levels of phosphatidylinositol (PI), phosphatidylinositol phosphate (PIP), and phosphatidylinositol bisphosphate ($PIP_2$) in human platelets (24,27). These observations support the notion that alterations in the phosphoinositide signaling pathway may be implicated in the pathophysiology of depression and/or the mode of action of antidepressant agents (5,26,52).

Several studies have hinted at links between the phosphoinositide system, PKC activity, and depression (28-30). However, these studies have not assessed the status of diacylglycerol production or metabolism as a potential target of disease pathology or pharmacological treatment. Diacylglycerol signaling is important as it is the endogenous regulator of PKC activity (Nishizuka, 1992). Among PLC-coupled receptors, however, significant differences exist in the ability of receptor activation to generate diacylglycerol, relative to IP, from receptor-mediated phospholipid hydrolysis (53-54).

It is recognized, therefore, to the extent that PI signaling or PKC activity may be involved in antidepressant drug action, that there is a significant need in the art for improvements in the area of treating depression with antidepressant agents that target cellular CDP-diacylglycerol. Specifically, the present invention is deficient in methods of screening for novel compounds that increase cellular CDP-diacylglycerol and methods of diagnosing and treating depression using the same. The present invention fulfills this long-standing need and desire in the art.

SUMMARY OF THE INVENTION

The present invention is directed, in part, to a method of identifying a compound effective to treat or to alleviate the symptoms of depression. This method comprises contacting a tissue having a CDP-diacylglycerol and phosphoinositide metabolic activity with a potential antidepressant compound and determining a level of CDP-diacylglycerol (CDP-DG) and a level of inositol phosphate in the tissue after contact therewith. An index value that is a ratio of CDP-diacylglycerol to inositol phosphate in the tissue is compared to a control index value, where a higher CDP-DG/IP index value in tissue treated with the compound indicates the potential compound has an antidepressant effect. The present invention is also directed to a related method comprising a further step of designing the antidepressive compound prior to screening, where the design is based on the structure of a tricyclic antidepressant, a selective serotonin reuptake inhibitor or an atypical antidepressant or on a structure of a compound structurally dissimilar thereto exhibiting an antidepressant effect or synthesizing a potential compound de novo. The present invention is directed to another related method comprising a further step of treating a subject having a depressive disorder with the antidepressant compound screened by this method.

The present invention also is directed to the compound screened by the method described supra. The present invention is directed to a related antidepressant compound effective to increase production of CDP-diacylglycerol and synthesis of inositol phosphate in a depression-relevant brain tissue or blood platelets upon contact therewith. The present invention is directed to a related synthetic compound effective to increase CDP-diacylglycerol synthase activity in a depression-relevant brain tissue or blood platelets upon contact therewith.

The present invention is directed further to a method of treating a depressive disorder in a subject. The method comprises administering one or more of the screened antidepressive compounds described supra to the subject, thereby treating the antidepressive disorder. The present invention is directed to a related method comprising a further step of administering one or more other known antidepressant drugs or other known compounds effective to increase an CDP-DG/IP index. The present invention is directed to another related method comprising a further step of determining a combination of the screened antidepressive compounds, the other antidepressant drugs or a combination thereof having maximum therapeutic efficacy against the depressive disorder. The present invention is directed to yet another related method comprising a further step of diagnosing the depressive disorder in a subject prior to treatment thereof.

The present invention is directed to a related method of treating depression in a subject. The method comprises administering to the subject an amount of a compound effective to increase CDP-diacylglycerol metabolism and phophatidylinositide synthesis in the subject, thereby treating the depression.

The present invention is directed further yet to a method of diagnosing a depressive disorder in a subject. The method comprises determining a basal CDP-DG/IP index that is the ratio of a level of CDP-diacylglycerol to a level of inositol phosphate in the subject and comparing the basal CDP-DG/IP index to a control CDP-DG/IP index, where a lower basal CDP-DG/IP index indicates the subject has a depressive disorder.

The present invention is directed further still to a method of predicting therapeutic efficacy of an antidepressant drug regimen in a subject having a depressive disorder. The method comprises administering a first selected drug regimen that is a combination of antidepressant drugs to the subject. A first CDP-DG/IP index value that is the ratio of a level of CDP-diacylglycerol (CDP-DG) to a level of inositol phosphate (IP) is determined in the subject after administration and the first index value is compared to the CDP-DG/IP index values of subsequently and individually administered combinations of other selected antidepressants where an ordering of the relative index values correlates to therapeutic efficacy of the drug regimen.

Other and further aspects, features and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized. The above may be better understood by reference to certain embodiments thereof which are illustrated in the appended drawings. These drawings form a part of the specification. It is to be noted; however, that the appended drawings illustrate preferred embodiments of the invention and therefore are not to be considered limiting in their scope.

DETAILED DESCRIPTION OF THE INVENTION

I. Definitions

Figure 1A:
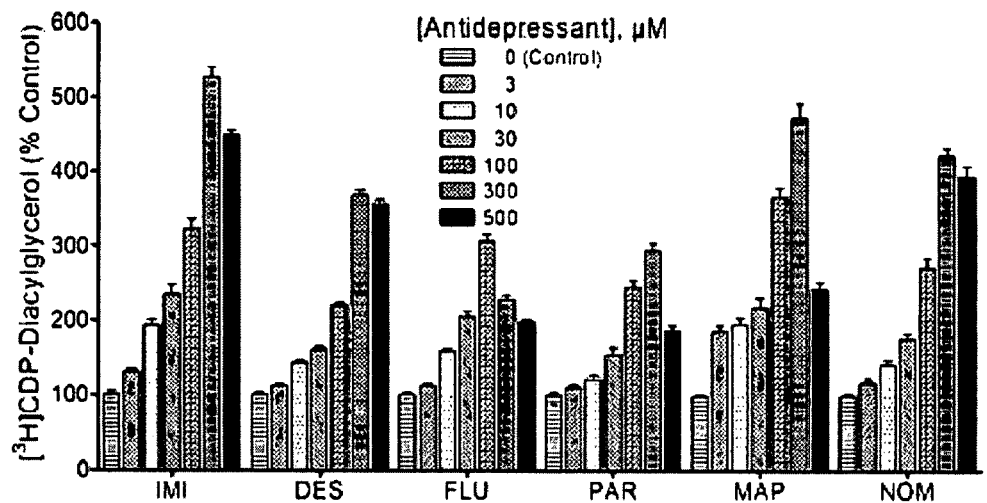
FIGS. 1A-1C demonstrate the effects of classic antidepressants on [$^3$H]CDP-diacylglycerol accumulation. Tissue slices prepared from the hippocampus (FIG. 1A), the frontal cortex (FIG. 1B) and the striatum (FIG. 1C) were prelabeled with [$^3$H]cytidine and incubated with various concentrations of either imipramine (IMI), desipramine (DES), fluoxetine (FLU), paroxetine (PAR), maprotiline (MAP), or nomifensine (NOM). After 90 min, tissue contents of [$^3$H] CDP-diacylglycerol were assayed. Each bar is the mean±SEM (N=9). Each drug stimulated significant concentration-dependent accumulations of CDP-diacylglycerol (ANOVA, $p<0.001$ for each drug). Based on posthoc Dunnett tests, all agents induced statistically significant CDP-diacylglycerol responses at the 3 or 10 μM concentrations, except for paroxetine in the hippocampus and imipramine in the striatum where the drug effects were not significant until the 30 μM and higher concentrations.

As used herein, the term "a" or "an", when used in conjunction with the term "comprising" in the claims and/or the specification may mean "one", but it is also consistent with the meaning of "one or more", "at least one", and "one or more than one". Some embodiments of the invention may consist of or consist essentially of one or more elements, method steps, and/or methods of the invention. It is contemplated that any method, compound, drug, or composition described herein can be implemented with respect to any other method, compound, drug, or composition described herein.

As used herein, the term "or" in the claims is used to mean "and/or" unless explicitly indicated to refer to alternatives only or the alternatives are mutually exclusive, although the disclosure supports a definition that refers to only alternatives and "and/or".

As used herein, the term "antidepressant drug or agent" refers to known compounds exhibiting an antidepressive effect or antidepressant effect on a subject having depression or a depressive disorder or mood disorder. Antidepressants may be, but not limited to, the tricyclic antidepressants, e.g., desipramine and imipramine, the selective serotonin reuptake inhibitors, e.g., fluoxetine and paroxetine, the atypical antidepressants, e.g., maprotiline and nomifensine, or de novo compounds SKF83959 or 6-chloro-7,8-dihydroxy-3-methyl-1-(3-methylphenyl)-2,3,4,5-tetrahydro-1H-3-benzazepine (55) and SKF38393 or (+/−)-1-phenyl-2,3,4,5-tetrahydro-(1H)-3-benzazepine-7,8-diol (56).

As used herein, the term "potential antidepressant compound" or "screened antidepressant compound" refers to a compound having, although not limited to, a similarity in structure, such as a derivative or analog, to a known antidepressant drug or agent" and/or a therapeutic ability to at least increase accumulation of cellular CDP-diacyglycerol and inositol phosphate and enhance synthesis of inositol phospholipids in brain tissue and/or blood platelets.

As used herein, the term "structural derivative" refers to a change to the structure of an original compound that conserves the functional aspects, i.e., biological activity, efficacy, and the like, of the original compound. For example, an original compound may be SKF83959 and a structural derivative may include an addition and/or a modification of the original benzazepine structure, such as changing halogen substituents, oxidation state, hydration, salt counterions, and the like.

As used herein, the term "CDP-DG/IP ratio" refers to the relative value of an index which is the quotient of a level of cellular CDP-diacylglycerol divided by a level of inositol phosphate in a tissue or cell or tissue cultures thereof, e.g., a mammalian brain tissue or blood platelets, a human brain tissue or blood platelets, or other cells or tissues having the ability to metabolize CDP-diacylglycerol and phosphoinositides. Levels may be determined, but are not limited to, using molar concentration or a radiolabel.

As used herein, the term "contacting" refers to any suitable method of bringing an antidepressant drug or agent or potential antidepressant compound into contact with a tissue or cell, e.g., a mammalian brain tissue or blood platelets or other blood cells, a human brain tissue, blood platelets or other blood cells, or other cells or tissues having the ability to metabolize CDP-diacylglycerol and phosphoinositides. In vitro or ex vivo this is achieved by exposing the tissue in a cell or tissue culture to the anti-depressive agent or potential antidepressive compound in a suitable medium. For in vivo applications, any appropriately known method of administration is suitable.

As used herein, the terms "effective amount" or "pharmacologically effective amount" or "therapeutically effective amount" are interchangeable and refer to an amount that results in an improvement or remediation of the symptoms of the depressive disorder or condition. The amount is sufficient to detectably and repeatedly to ameliorate, reduce, minimize, or limit the extent of the depressive disorder or condition or the symptoms thereof. Those of skill in the art understand that the effective amount may improve the patient's or subject's condition, but may not be a complete cure of the depressive disorder and/or condition.

As used herein, the term "depressive disorder" or "mood disorder" refers to clinical depression, major depression, unipolar depression, reactive depression, endogenous depression, dysthymia, or bipolar disorder. As used herein, the term "subject" refers to any target of the treatment, preferably a mammal, more preferably a human.

II. Present Invention

In one embodiment of the present invention, there is provided a method of identifying a compound effective to treat or alleviate the symptoms of depression, comprising contacting a tissue having a CDP-diacylglycerol and phosphoinositides metabolic activity with a potential antidepressant compound;

determining a level of CDP-diacylglycerol (CDP-DG) and a level of inositol phosphate in the tissue after contact therewith; and comparing an index value that is a ratio of CDP-diacylglycerol to inositol phosphate in test tissue to a control index value, wherein a higher CDP-DG/IP index value in tissue treated with the compound indicates the potential compound has an antidepressant effect.

Further to this embodiment, the method comprises designing the potential antidepressive compound prior to screening, where the design is based on the structure of a tricyclic antidepressant, a selective serotonin reuptake inhibitor or an atypical antidepressant or on a structure of a compound structurally dissimilar thereto exhibiting an antidepressant effect or synthesizing a potential compound de novo. Examples of a tricyclic antidepressant is desipramine or imipramine. Examples of a selective serotonin reuptake inhibitor are fluoxetine or paroxetine. Examples of an atypical antidepressant are maprotiline or nomifensine. Other atypical antidepressants may be SKF83959, or SKF38393 or a structural derivative thereof. In another further embodiment the method comprises treating a subject having a depressive disorder with the compound screened by the method.

In another embodiment of the present invention, there is provided a compound screened by the method described supra. In a related embodiment there is provided a synthetic antidepressant compound effective to increase production of CDP-diacylglycerol and synthesis of inositol phosphate in a depression-relevant brain tissue or blood platelets upon contact therewith. In both embodiments, the screened compound and the synthetic antidepressant compound may be an analog or derivative of a tricyclic antidepressant, a selective serotonin reuptake inhibitor or an atypical antidepressant. Examples of these antidepressants are described supra. In another related embodiment there is provided a synthetic compound effective to increase CDP-diacylglycerol synthase activity in a depression-relevant brain tissue, blood platelets or other blood cells upon contact therewith.

In yet another embodiment of the present invention, there is provided a method of treating a depressive disorder in a subject, comprising administering one or more of the screened compounds described supra to the subject, thereby treating the antidepressive disorder. Further to this embodiment the method comprises administering one or more other known antidepressant drugs or other known compounds effective to increase an CDP-DG/IP index. The antidepressant drugs may be a tricyclic antidepressant, a selective serotonin reuptake inhibitor or an atypical antidepressant with specific examples thereof as described supra. The other known compound is SKF83959 or SKF38393 or a structural derivative thereof. Examples of the depressive disorder include but are not limited major depression, unipolar depression, bipolar depression, reactive depression, endogenous depression or dysthymic disorder.

In another further embodiment the method comprises diagnosing the depressive disorder in a subject prior to treatment thereof. In this further embodiment diagnosing the depressive disorder comprises determining a level of CDP-diacylglycerol and a level of inositol phosphate in the subject; and comparing an index value that is a ratio of CDP-diacylglycerol to inositol phosphate (IP) in the subject to a control index value, wherein a lower CDP-DG/IP index value indicates the subject has a depressive disorder.

In yet another further embodiment, the method comprises determining a combination of the screened antidepressive compounds, the other antidepressant drugs or a combination thereof having maximum therapeutic efficacy against the depressive disorder. Determining the combination of antidepressant drugs comprises administering a first selected combination of antidepressants to the subject; determining a first index value that is a level of CDP-diacylglycerol (CDP-DG) and of inositol phosphate (IP) in the subject after administration of the antidepressant combination; and comparing the first index value to the CDP-DG/IP index values of subsequently and individually administered combinations of other antidepressants; wherein the combination having the highest CDP-DG index correlates to a maximum therapeutic efficacy.

In a related embodiment, there is provided a method of treating depression in a subject, comprising administering a CDP-diacylglycerol-increasing amount of a compound to the subject, where the compound increases CDP-diacylglycerol metabolism in the subject, thereby treating the depression. Representative examples of the compound are maprotiline, nomifensine, SKF83959, SKF38393, or a structural derivatives thereof.

In yet another embodiment, there is provided a method of diagnosing a depressive disorder in a subject, comprising determining a basal CDP-DG/IP index that is the ratio of a level of CDP-diacylglycerol to a level of inositol phosphate in the subject; and comparing the basal CDP-DG/IP index to a control CDP-IP index, where a lower basal CDP-DG/IP index indicates the subject has a depressive disorder. In this related embodiment the diagnosis may be predictive of the onset of a depressive disorder. The depressive disorder may be as described infra.

In still another embodiment of the present invention there is provided method of predicting therapeutic efficacy of an antidepressant drug regimen in a subject having a depressive disorder, comprising administering a first selected drug regimen that is a combination of antidepressant drugs to the subject; determining a first CDP-DG/IP index value that is the ratio of a level of CDP-diacylglycerol (CDP-DG) to a level of inositol phosphate (IP) in the subject after administration; comparing the first index value to the CDP-DG/IP index values of subsequently and individually administered combinations of other selected antidepressants; wherein an ordering of the relative index values correlates to therapeutic efficacy of the drug regimen. In this embodiment, the combination of antidepressant drugs may comprise a tricyclic antidepressant (s), a selective serotonin reuptake inhibitor(s) or an atypical antidepressant(s) or derivatives or analogs thereof or a novel synthetic antidepressant compound designed de novo that increases production of CDP-diacylglycerol and synthesis of inositol phosphate in a depression-relevant brain tissue or blood platelets or other blood cells. The examples of a tricyclic antidepressant, a selective serotonin reuptake inhibitor and an atypical antidepressant are as described supra. Also, the depressive disorder may be as described supra.

The present invention demonstrates that antidepressants belonging to diverse chemical and pharmacological classes acutely increase the formation of CDP-diacylglycerol (CDP-DG), a metabolic derivative of diacylglycerol, which effect may translate to enhanced resynthesis of the phosphatidylinositides. Phosphatidylinositides are metabolically used either as substrates for PLC or as precursors to the phosphatidylinositol-3-kinase (PI-3-K)/Akt signaling cascade. It is contemplated, therefore, that an acute molecular action of antidepressant agents that facilitates the conservation or supplementation of cellular phosphatidylinositides may contribute to the therapeutic mechanism of these medications in depression-relevant brain regions.

It is also contemplated that known antidepressants may exert tandem neurochemical effects by increasing synaptic monoamine concentrations and by producing phosphoinositide substrates used in $5HT_2$ receptor signaling. This combination of actions may constitute the mechanism of at least the acute behavioral effects of antidepressant medications and, thereby, may implicate aberrant phospholipid signaling in the neuropathology of depressive disorder.

Thus, provided herein is a method of screening for potential antidepressant compounds. Potential antidepressant agents are distinguished from other compounds that enhance phosphoinositide signaling by the relative value of the CDP-DG/IP index. An increase in the CDP-DG/IP index compared to a control index is indicative that the potential antidepressant compound may exhibit antidepressant effects by at least increasing cellular CDP-diacylglycerol in a subject with a depressive or mood disorder. Cellular levels of CDP-diacylglycerol and inositol phosphate may be determined in brain tissue, blood platelets or other blood cells, cultured cells or combination of tissues in the presence and absence of potential antidepressant compounds using assay methods known and standard in the art.

As such, the antidepressant compounds identified by the screening method also are provided. It is contemplated that these screened antidepressant compounds may be derivatives or analogs of known antidepressant drugs or agents as described herein. Alternatively, the antidepressant compounds may have a novel synthetic structure designed de novo using standard methods of chemical design known in the art, for example, but not limited to, computer aided drug design.

Compositions, Pharmaceutical Formulations and Methods of Treating

The present invention also contemplates therapeutic or treatment methods employing compositions comprising the screened antidepressant compounds disclosed herein, that is, compositions comprising the known antidepressant drugs and/or the screened antidepessant compounds provided herein. Preferably, these compositions include pharmaceutical compositions comprising a therapeutically effective amount of one or more of the active compounds or substances along with conventional non-toxic, physiologically or pharmaceutically acceptable carriers or vehicles suitable for the method of administration.

As used herein, the term "pharmaceutically acceptable" carrier or vehicle means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alpha-tocopherol and the like; and the metal chelating agents such as citric acid, ethylenediamine tetraacetic acid (EDTA), sorbitol, tartaric acid, phosphoric acid and the like.

Treatment methods will involve treating an individual with an effective amount of a composition containing the screened antidepressant compound and/or known antidepressant drug or related compounds thereof. More specifically, it is envisioned that the treatment with the antidepressant compounds and/or antidepressant drugs or related-compounds thereof will increase production of CDP-diacylglycerol and synthesis of inositol phospholipids in depression-relevant brain tissues or blood platelets or other blood cells to produce a beneficial result in a depressive or mood disorder.

The effective amount of the screened antidepressant compound and/or known antidepressant drug or related compounds thereof to be used are those amounts effective to produce these beneficial results in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value. One of skill in the art realizes that the effective amount of the screened antidepressant compound and/or known antidepressant drug or related compounds thereof can be the amount that is required to achieve the desired result: conserving or supplementing cellular phosphatidylinositides, and increased production of CDP-diacylglycerol etc.

As is well known in the art, a specific dose level of active compounds such as the screened antidepressant compound and/or known antidepressant drug or related compounds thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

Administration of the compositions comprising the screened antidepressant compound and/or known antidepressant drug or related compounds thereof of the present invention to a patient or subject will follow general protocols for the administration of therapies used in treatment of depressive or mood disorders taking into account the toxicity, if any, of the antidepressant compound and/or known antidepressant drug or related compounds.

Dose Determinations

By a "therapeutically or pharmacologically effective amount" or simply "effective amount" of the active agents, i.e., antidepressive compounds and/or drugs or other related compounds described herein, is meant a sufficient amount thereof to treat a depressive or other mood disorder at a reasonable benefit/risk ratio applicable to any medical treatment. It will be understood, however, that the total daily usage of the active agents and compositions of the present invention will be decided by the attending physician within the scope of sound medical judgment. The specific therapeutically effective dose level for any particular patient will depend upon a variety of factors including the depressive or mood disorder being treated and the severity of the same; activity of the specific active agent employed; the specific composition employed; the age, body weight, general health, sex and diet of the patient; the time of administration, route of administration, and rate of excretion of the specific compound employed; the duration of the treatment; drugs used in combination or coinciding with the specific compound employed; and like factors well known in the medical arts.

Toxicity and therapeutic efficacy of such compounds can be determined by standard pharmaceutical procedures in cell assays or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell or tissue culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell based assays. A dose may be formulated in animal models to achieve a circulating plasma concentration range that includes the IC50, i.e., the concentration of the test compound which achieves a half-maximal inhibition of symptoms, as determined in cell culture. Such information can be used to more accurately determine useful doses in humans. Levels in plasma may be measured, for example, by high performance liquid chromatography.

The total daily dose of the active compounds of the present invention administered to a subject in single or in divided doses can be in amounts, for example, from 0.01 to 25 mg/kg body weight or more usually from 0.1 to 15 mg/kg body weight. Single dose compositions may contain such amounts or submultiples thereof to make up the daily dose. In general, treatment regimens according to the present invention comprise administration to a human or other mammal in need of such treatment from about 1 mg to about 1000 mg of the active substance(s) of this invention per day in multiple doses or in a single dose of from 1 mg, 5 mg, 10 mg, 100 mg, 500 mg or 1000 mg.

Formulations and Administration

The compounds of the present invention may be administered alone or in combination or in concurrent therapy with other agents which affect the targeted cell(s). Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers, such as polylactide-polyglycoside. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions, which are compatible with body tissues.

Suppositories for rectal administration of the drug can be prepared by mixing the drug with a suitable non-irritating excipient, such as cocoa butter and polyethylene glycol which are solid at ordinary temperature but liquid at the rectal temperature and will, therefore, melt in the rectum and release the drug.

Solid dosage forms for oral administration may include capsules, tablets, pills, powders, gelcaps and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient (s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. Transdermal patches have the added advantage of providing controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

The method of the present invention employs the compounds identified herein for both in vitro and in vivo applications. For in vivo applications, the invention compounds can be incorporated into a pharmaceutically acceptable formulation for administration. Those of skill in the art can readily determine suitable dosage levels when the invention compounds are so used. As employed herein, the phrase "suitable dosage levels" refers to levels of compound sufficient to provide circulating concentrations high enough to effectively increase production of CDP-diacylglycerol and synthesis of inositol phospholipids in a depression-relevant brain tissue, blood platelets or other blood cells in vivo.

In accordance with a particular embodiment of the present invention, compositions comprising one or more antidepressant compounds, optionally including one or more known antidepressant drugs, or related compounds and a pharmaceutically acceptable carrier are contemplated. Exemplary pharmaceutically acceptable carriers include carriers suitable for oral, intravenous, subcutaneous, intramuscular, intracutaneous, topical or transdermal and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use. The active compound is admixed under sterile conditions with a pharmaceutically acceptable carrier and any needed preservatives or buffers as may be required.

The treatments may include various "unit doses." Unit dose is defined as containing a predetermined quantity of the therapeutic composition calculated to produce the desired responses in association with its administration, e.g., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

Thus, methods of diagnosing a depressive disorder in a subject, preferably a human, are provided. Brain, platelet or other blood cell levels of CDP-diacylglycerol are measured to aid diagnosis of an active or impending depressive episode. A determination of an abnormal CDP-diacylglycerol signaling in the subject may be indicative of a depressive or mood disorder. Therefore, the CDP-DG/IP index may be a useful diagnostic tool in the diagnosis of a depressive or mood disorder.

In addition, methods of treating a depressive or mood disorder in a subject are provided. A pharmacologically effective or therapeutically effective amount of one or more of the screened antidepressive compounds described herein or a pharmaceutical composition comprising the same is administered to the subject. Alternatively, treatment may comprise a combination of the screened antidepressive compound(s) and one or more known antidepressants or pharmaceutical compositions thereof. As such, treatment by, for example, but not limited, to atypical antidepressants or structural derivatives thereof provide a therapeutic effect of at least increasing CDP-diacylglycerol metabolism.

Further provided is a method of predicting the potential effectiveness of antidepressant combinations for various patients based on the basal CDP-DG/IP ratio of each patient. An increase in the CDP-DG/IP index compared to the basel index of current or novel antidepressant compounds may be predictive of antidepressant effects in a subject. A successful regimen may comprise a combination of the known tricyclic antidepressants, the known selective serotonin reuptake inhibitors and the known atypical antidepressants and/or the novel antidepressant compounds screened as described herein.

The following examples are given for the purpose of illustrating various embodiments of the invention and are not meant to limit the present invention in any fashion.

Example 1

Animals

Male Sprague-Dawley rats, weighing between 225 g-300 g, were obtained from Zivic Laboratories (Zelienople, Pa.) and housed in climate-controlled facilities with a 12-h light/dark cycle for at least 3 days before use. The animals were caged in groups of three and allowed free access to food and water.

Drugs and Chemicals

Antidepressant compounds and buffer reagents were purchased from Sigma-Aldrich (St. Louis, Mo.). SKF38393 was from the NIMH Chemical Synthesis Program (NIMH, Bethesda, US). Nomifensine was first dissolved in 0.2% tartaric acid and SKF38393 in distilled water before either drug was diluted to use concentrations in assay buffer. Other drugs were prepared fresh in HEPES bicarbonate assay buffer (HBB) (57). Each experiment was performed on multiple occasions using fresh preparations of drugs. Protein was assayed by the Bradford method using BioRad protein assay reagents (BioRad, Hercules, Calif.).

Measurement of CDP-Diacylylycerol Accumulation

Accumulation of CDP-diacylglycerol was measured in brain slice preparations by taking advantage of the CTP-phosphatidate transfer reaction (58-60). Briefly, male Sprague-Dawley rats weighing between 225 and 300 g were rapidly decapitated and the brains removed and rinsed in calcium-free HBB (58,61). Brain regions of interest, including the hippocampus, prefrontal cortex and striatum, were quickly dissected out and 350 µm prisms prepared using a McIlwain tissue chopper (61). The slices were washed with calcium-free HBB and pre-incubated for 45 minutes at 37° C. Slice aliquots of approximately 300 µg protein then were incubated with 1.5 µCi of 5-[$^3$H]cytidine (20 Ci/mmol; American Radiolabeled Chemicals, St. Louis, Mo.) in order to generate an endogenous pool of radiolabeled cytidine triphosphate (CTP) for feeding into the CTP:phosphatidate transfer reaction (58).

Following addition of 5 mM LiCl, test drugs or buffer were added for a total volume of 250 µl and incubation continued for 60 or 90 min as indicated. Reactions were terminated by addition of 1.5 ml chloroform-methanol-1M HCl (100:200: 1). Formed lipids were extracted by liquid partitioning in chloroform followed by centrifugation at 1000×g for 5 min to separate the liquid phases. Aliquots of the organic phase were transferred quantitatively into scintillation vials, dried at room temperature and redissolved in Biosafe scintillation cocktail. Radioactivity in this lipid fraction was determined by liquid scintillation spectrometry, and corresponds to [$^3$H] CDP-DG (54,58,62).

Measurement of Inositol Phospholipid Resynthesis

Brain tissues were prepared and were incubated as described above for assaying CDP-DG, except that 1.5 µCi of [$^3$H]inositol (20 Ci/mmol; American Radiolabeled Chemicals, St. Louis, Mo.) was used instead of [$^3$H]cytidine to label the slices. Following the labeling incubation, drugs were added and allowed to act for 60 or 90 min as indicated. Samples were extracted with chloroform-methanol-1M HCl (100:200:1), partitioned with chloroform into aqueous and organic phases, and aliquots of the organic phase dried and assessed for radioactivity that corresponded to the inositol phospholipids. It was not necessary to attempt to separate the multiple phosphorylated or isomeric forms of these phospholipids. Hence, the data potentially represent the mix of phosphatidylinositol, phosphatidylinositol-4-phosphate, and phosphatidylinositol 4,5-bisphosphate in any of their positional isomeric forms. Based on the levels of the phospholipids present at the start of drug treatment, a subsequent decrease is seen as depletion, whereas an increase in the [$^3$H]inositol-labeled pool of the phospholipids is considered to represent further phospholipid synthesis or resynthesis (59,63).

Measurement of Inositol Phosphate Accumulation

To measure the levels of IPs formed, tissues were treated exactly as in the PI synthesis assays described herein, including the use of [$^3$H]inositol for prelabeling of the PI pool. The 250 µl reactions were terminated by mixing the samples with 1.5 ml of chloroform-methanol-1 M HCl (100:200:1). Following chloroform-mediated partitioning of the extracts as described (57), aliquots of the aqueous phase were analyzed for the content of [$^3$H]IPs by Dowex anion exchange chromatography (57,61). An IP fraction was collected from the eluate and the solution converted into a gel by use of Scintisafe Gel (Fisher Scientific, Pittsburgh, Pa.). The amounts of IP-associated radioactivity in the samples were then measured by liquid scintillation spectrometry.

Forced Swim Test

The forced swim test (FST) was applied with some modifications. Rats were transferred to the testing room between 9:00-10:00 AM and allowed at least an hour before being placed individually into translucent polypropylene cylinders (46 cm tall×25 cm in diameter) containing 27 cm depth of water maintained at 25° C. (64-65). After 15 min in the water, the rats were removed, toweled, and allowed to dry in a warm environment before being returned to their home cage. This acclimation step was repeated after 24 h, with the exposure time reduced from 15 to 5 min. Preliminary testing showed that the double acclimation exposure produced more consistent results among animals in each test group (lower variability) than the conventional single acclimation.

During the second acclimation exposure, the duration of immobility was recorded for each animal. While the initial intent was to eliminate animals that did not attain immobility within 5 min, in practice all animals used in the present experiments passed this test at the second acclimation session. To adjudge that a rat had become immobile, the animal had to float passively in the water in a slightly hunched, but upright position, making only minimal movements necessary to keep its head above the water (65-66).

On the third day when animals were to undergo experimental assessment, saline or the indicated antidepressant agents were administered i.p. at 3 h and at 1 h before behavioral testing. The drugs were dissolved in distilled-deionized water and diluted in saline. Control subjects received 0.9% saline. Drugs were freshly made before use and injected in a constant volume of 1 ml/kg except for fluoxetine which was given at a volume of 5 ml/kg. Neomycin was prepared as a solution in normal saline and injected into the tail vein 2 h prior to testing, that is, 1 h between the first and second administrations of the test drug. This approach has been reported to be effective in inhibiting endogenous brain PI metabolism for behavioral studies (67), although other approaches such as intracerebroventricular injection have also been used (68-69). Data were analyzed by one-way analysis of variance (ANOVA). Conclusions of mean differences were drawn when the calculated p-values were less than 0.05.

Data Analysis

Data from the various experiments were normalized relative to the respective control or basal measurements, and then pooled for analysis. Data were tested by an appropriate analysis of variance (ANOVA) using SPSS software (SPSS, Chicago, Ill., USA). Where warranted, the ANOVAs were followed by post hoc analyses using the Dunnett test to compare various treatment means to their respective controls. Statistical comparisons were considered significant at p<0.05 or better.

Example 2

Chemically Diverse Antidepressant Agents Increase CDP-Diacylglycerol Production

Diacylglycerol released from phospholipid breakdown is normally rapidly phosphorylated to produce phosphatidic acid. In the presence of [$^3$H]cytidine-labeled CTP, however, the phosphatidic acid is converted to radiolabeled CDP-DG, which can be extracted and separated away from other labeled metabolites and subsequently quantified. Rat brain cerebrocortical, hippocampal, and striatal slices prelabeled with [$^3$H]

cytidine were incubated with various concentrations of selected antidepressant agents in the presence of LiCl, and the yield of CDP-diacylglycerol analyzed. Data for each drug were separately analyzed before they were normalized and collated together for graphical presentation as shown.

Figure 1B:
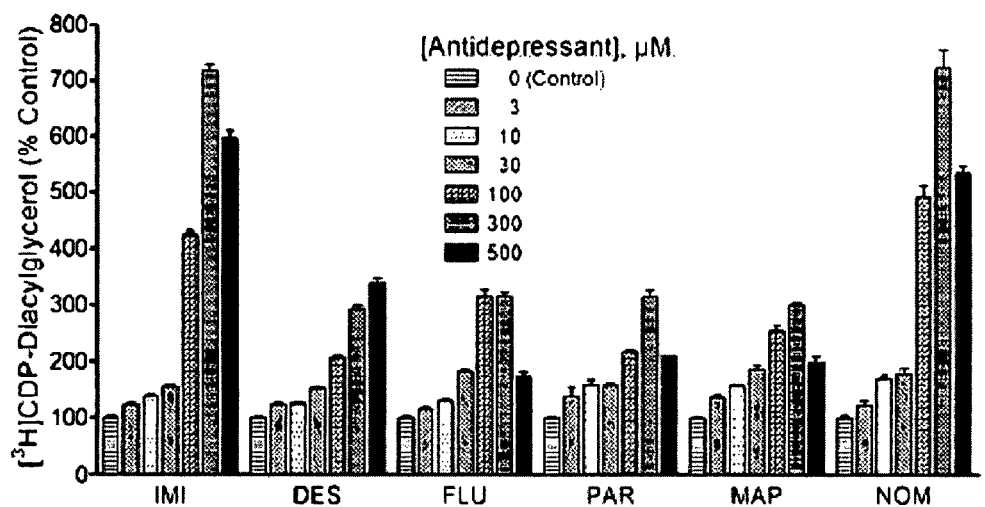
Figure 1C:
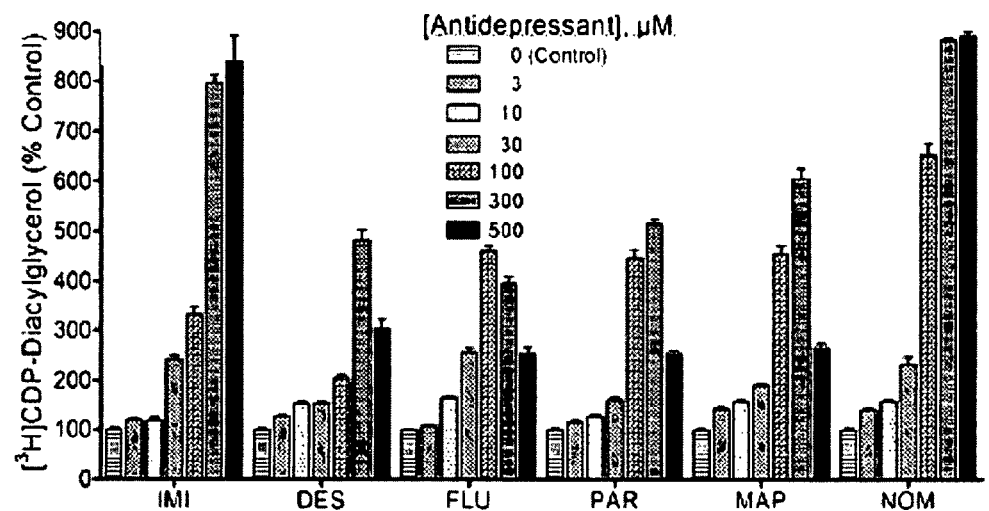

The classical antidepressants imipramine and desipramine, the selective serotonin reuptake inhibitors fluoxetine and paroxetine and the atypical agents maprotiline and nomifensine each significantly and dose-dependently enhanced the accumulation of [$^3$H]CDP-DG in rat hippocampal, prefrontal cortical, and striatal slices (FIGS. 1A-1C). While concentrations ranging from 0.1 to 1000 μM were tested, only those concentrations lying between the minimal that gave statistically significant effects for any agent (1-3 μM) and the maximally effective concentrations (100-500 μM) are shown. Statistically significant effects were obtained at concentrations as low as 3-10 μM in the hippocampus or prefrontal cortex, while maximal effects were achieved at the 100 μM concentration of fluoxetine or 300 μM concentrations of most other agents. For all agents, test concentrations greater than 300 μM resulted in CDP-DG effects that were either statistically similar to, or significantly lower than, the effects observed at 100 μM for fluoxetine or 300 μM for the other agents. This reduction in response with increasing concentration after attaining maximal responses was more apparent with the SSRIs, fluoxetine and paroxetine, than with the tricyclic agents.

Figure 2A:
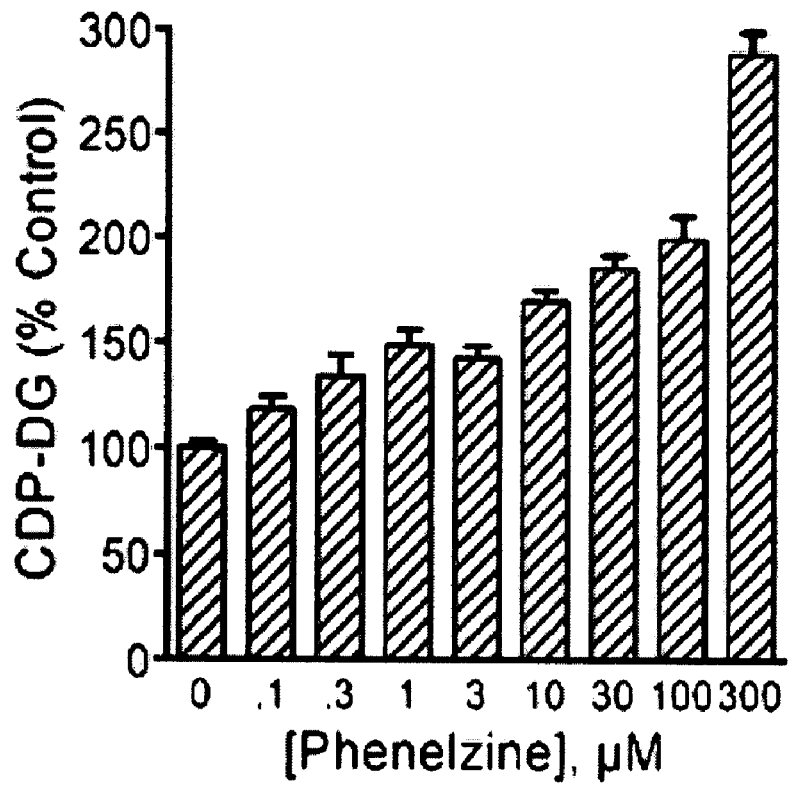
FIGS. 2A-2B demonstrate the effects of phenelzine and hydralazine on [$^3$H]CDP-diacylglycerol accumulation. Cortical slices were tested with indicated concentrations of phenelzine (FIG. 2A) or hydralazine (FIG. 2B) and CDP-diacylglycerol levels similarly analyzed as outlined under FIGS. 1A-1C. Each bar is the mean±SEM (N=9). Both drugs stimulated concentration-dependent accumulations of CDP-diacylglycerol (ANOVA, $p<0.001$ for each drug).
Figure 2B:
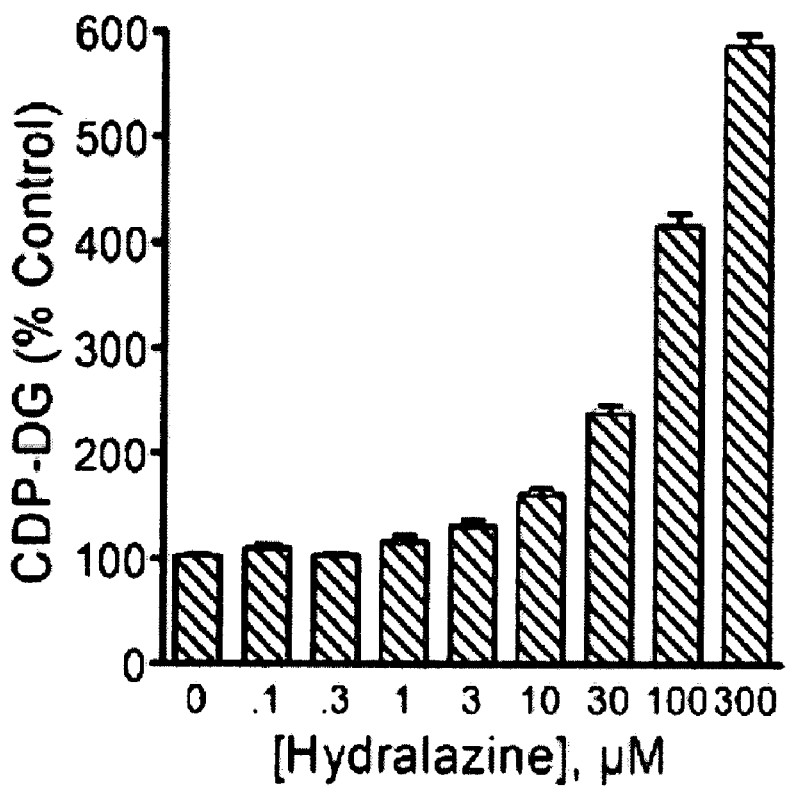

Similar to the effects exhibited by the classical antidepressant agents, the monoamine oxidase inhibitors (MAOIs), phenelzine and hydralazine, produced robust effects on CDP-DG accumulation in frontal cortex slices (FIGS. 2A-2B), while tranylcypromine had statistically significant but modest effects. While the effects of phenelzine achieved significance at 1 μM (Dunnett's, p<0.01), those of hydralazine became significant at the 10 μM and higher concentrations.

Also, a range of other psychotropic compounds were tested to estimate the extent to which the CDP-DG response may characterize compounds with antidepressive activity. No significant effects or concentration-related effects on CDP-diacylglycerol accumulation in rat cerebrocortical slices were observed with the MAOIs pargyline, selegiline, or quinacrine, the antipsychotics chloropromazine, haloperidol, sulpiride, and flupenthioxol and the anticonvulsants or anxiotytics phenobarbital, phenyloin, diazepam, nitrazepam, benztropine, phenylephrine, chlordiazepoxide, and hydroxylamine. Agents were tested at multiple concentrations ranging from 0.1-300 μM. Data from up to three separate runs were normalized and pooled for analysis by One-Way ANOVA.

Among the brain regions, the hippocampus appeared to be more sensitive, i.e., greater response magnitudes at lower concentrations, whereas the striatum gave slightly more robust, i.e., maximally attained, effects. The drug responses were statistically dose-dependent for all effective agents in each tissue, but there were noticeable differences in potency or efficacy among the compounds as shown in the data. Thus, diverse antidepressant agents can acutely induce CDP-DG synthesis in depression-relevant regions of the rat brain Example 3

Figure 3A:
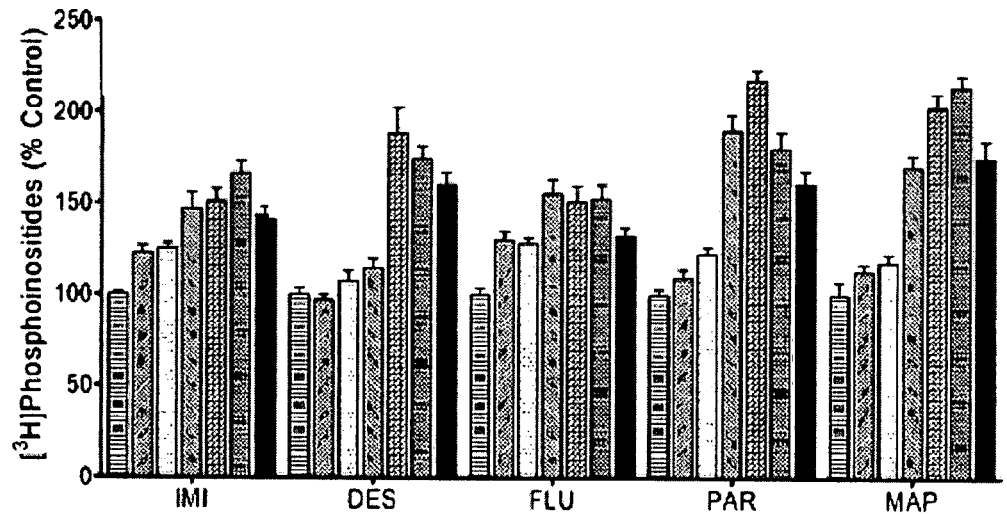
FIGS. 3A-3C demonstrate the effects of various classic antidepressants on [$^3$H]phosphatidylinositide synthesis. Tissue slices prepared from the hippocampus (FIG. 3A), the frontal cortex (FIG. 3B) and the striatum (FIG. 3C) and prelabeled with [$^3$H]inositol were incubated with various concentrations of either imipramine (IMI), desipramine (DES), fluoxetine (FLU), paroxetine (PAR), or maprotiline (MAP). After 90 min, [$^3$H]inositol phospholipids were extracted and assayed as a total pool of extractable phosphatidylinositides. Each bar is the mean±SEM (N=9). Each drug stimulated significant and concentration-dependent increases in [$^3$H] inositol phospholipid synthesis (ANOVA, $p<0.001$ for each drug). From the subsequent posthoc Dunnett tests, all agents induced statistically significant CDP-diacylglycerol responses at the 3 or 10 μM and higher concentrations.
Figure 3B:
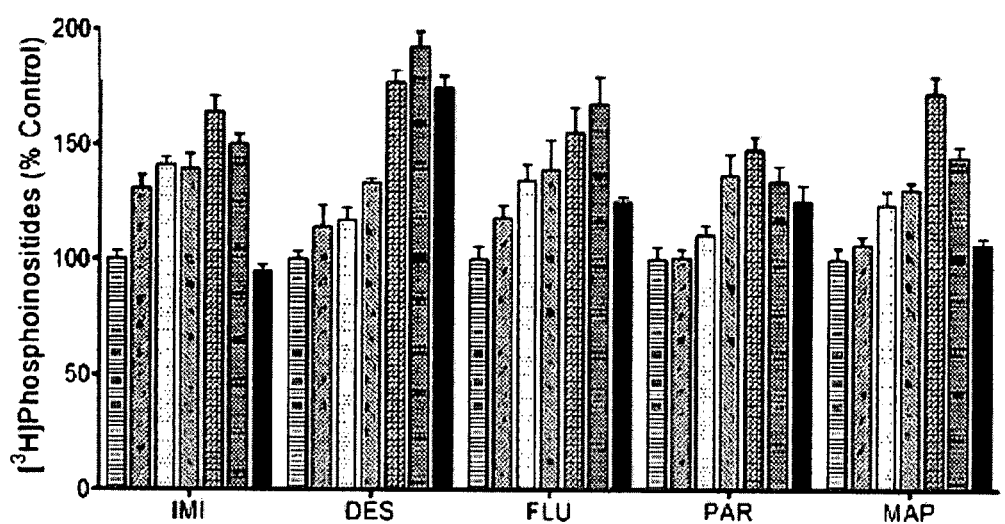
Figure 3C:
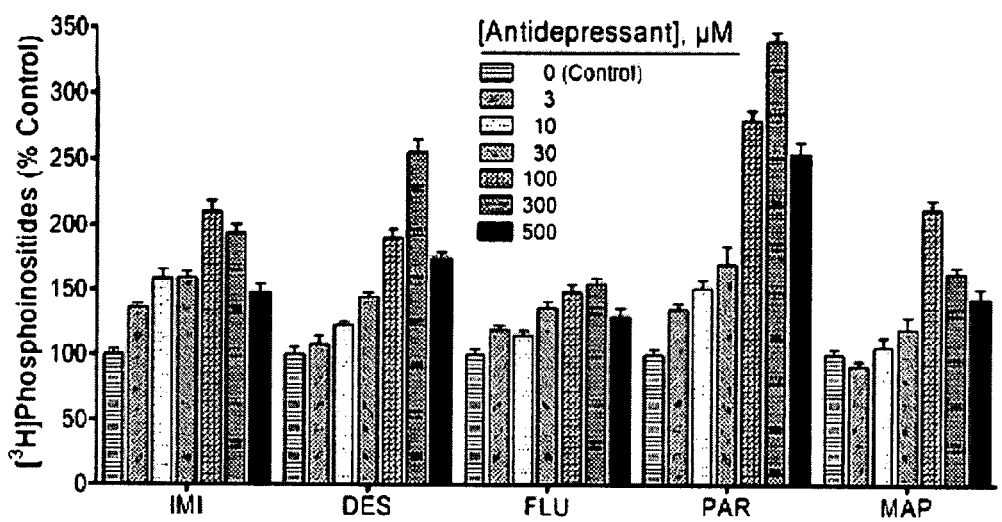
Figure 4A:
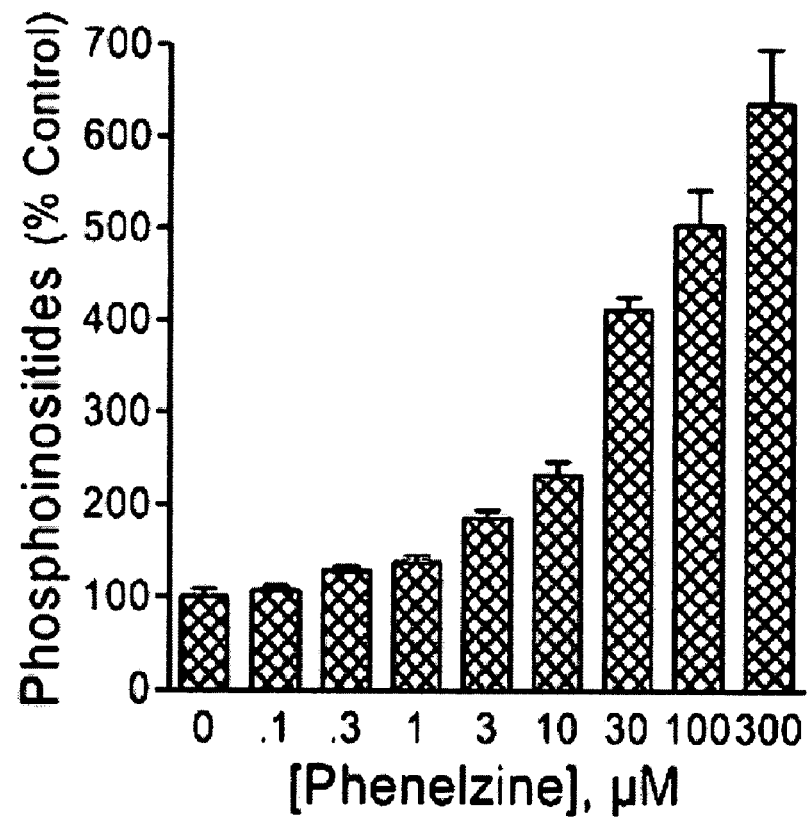
FIGS. 4A-4B demonstrate the effects of phenelzine (FIG. 4A) and hydralazine (FIG. 4B) on [$^3$H]phosphatidylinositide synthesis. Rat cortical slices were prepared and tested with indicated concentrations of phenelzine or hydralazine as in FIGS. 3A-3C. Each bar is the mean±SEM (N=9). Phenelzine and hydralazine each stimulated significant and concentration-dependent increases in [$^3$H]inositol phospholipid synthesis (ANOVA, $p<0.001$ for each drug).
Figure 4B:
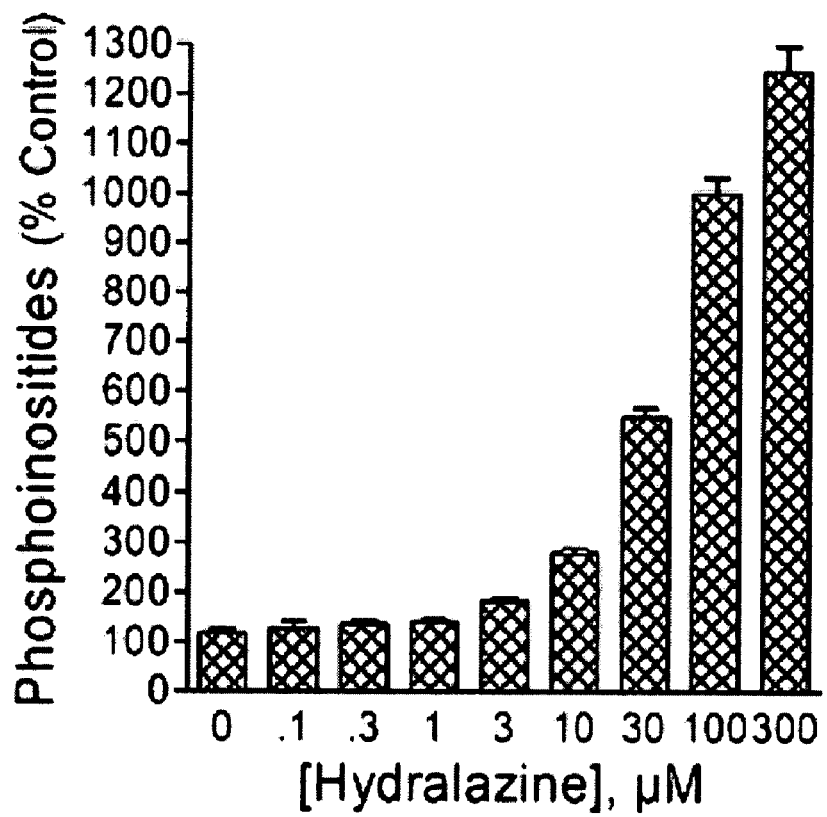

Antidepressant-Induced CDP-Diacylglycerol Formation Translates into Increased Phosphoinositide Synthesis To test if the antidepressant-enhanced CDP-DG translates into increased synthesis of the PIs, brain slice preparations were labeled with [$^3$H] inositol and incubated in the presence of various antidepressant agents. Results of the subsequent uptake and conversion of [$^3$H] inositol into inositol phospholipids are shown in FIGS. 3A-3C. Imipramine, desipramine, fluoxetine, paroxetine, and maprotiline each significantly increased [$^3$H]inositol labeling of PIs in the tested brain regions. MAOIs that were effective in inducing CDP-DG production also showed enhanced effects on PI resynthesis (FIGS. 4A-4B), whereas other MAOIs that were ineffective on CDP-DG were equally ineffective in increasing PI resynthesis. Thus, the increased mobilization or recapture of CDP-DG by the antidepressant agents translates into increased regeneration of PI signaling substrates.

Example 4

Antidepressant Agents Generally Enhance Inositol Phosphate Accumulation

Figure 5A:
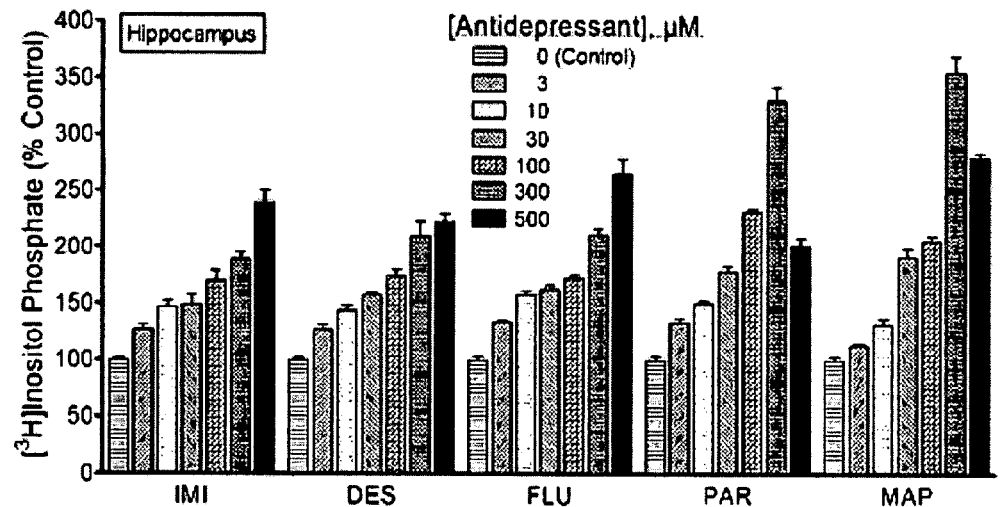
FIGS. 5A-5C demonstrate the effects of diverse antidepressants on [$^3$H]inositol phosphate accumulation. Tissue slices from the hippocampus (FIG. 5A), the frontal cortex (FIG. 5B) and the striatum (FIG. 5C) were prepared and tested as in FIGS. 3A-3C except that the tissue contents of [$^3$H]inositol phosphates were assayed by Dowex anion exchange chromatography as described herein. Each bar is the mean±SEM (N=9). Each antidepressant agent induced significant concentration-dependent accumulations of inositol phosphate (ANOVA, $p<0.001$ for each drug).
Figure 5B:
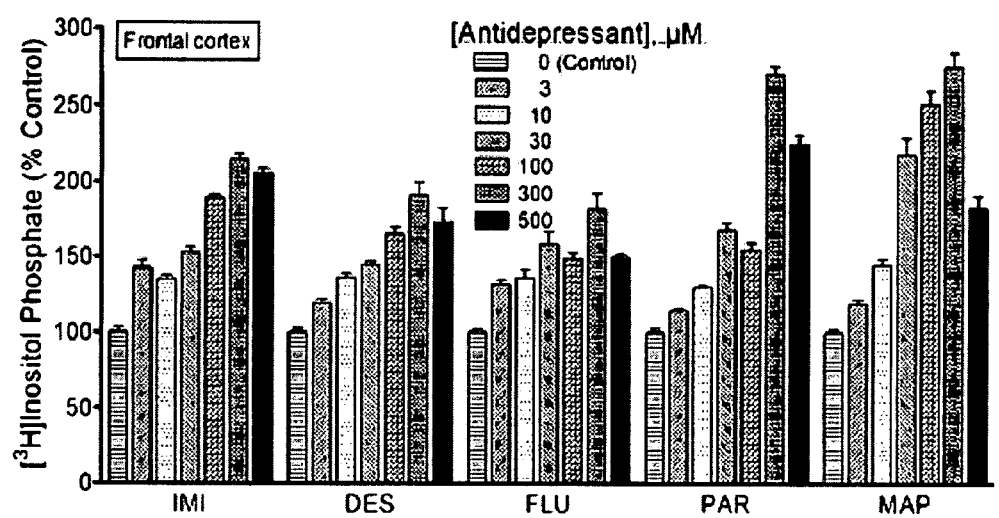
Figure 5C:
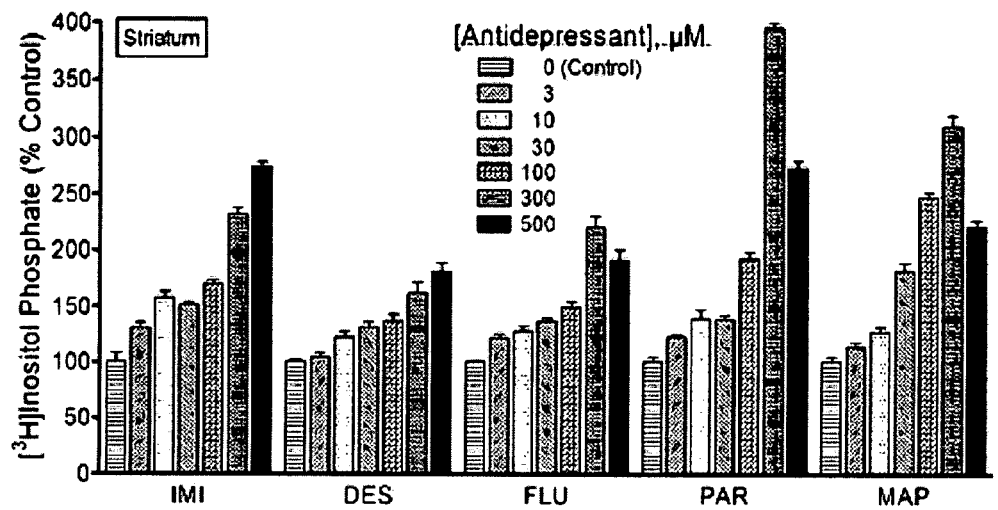

To test if resynthesized PIs might contribute to enhanced IP accumulation, agents tested for effects on CDP-DG were also tested in a standard IP assay. Across a concentration range of 3-300 μM, imipramine, desipramine, fluoxetine, paroxetine, and maprotiline significantly and dose-dependently stimulated the accumulation of IPs in each brain region (FIGS. 5A-5C). Significant drug effects were generally evident at concentrations of 3-10 μM, while maximal effects were observed at 100-300 μM. With imipramine tested in the hippocampus and striatum as the only possible exceptions, test concentrations greater than 300 μM resulted in IP effects that were either statistically similar to, or significantly lower than, the effects observed at the corresponding 300 μM concentration. In general, drug concentrations greater than 300-500 μM were associated with IP levels that were significantly lower than effects at 100-300 μM concentrations, possibly reflecting toxicity from excessive stimulation.

Example 5

Figure 6A:
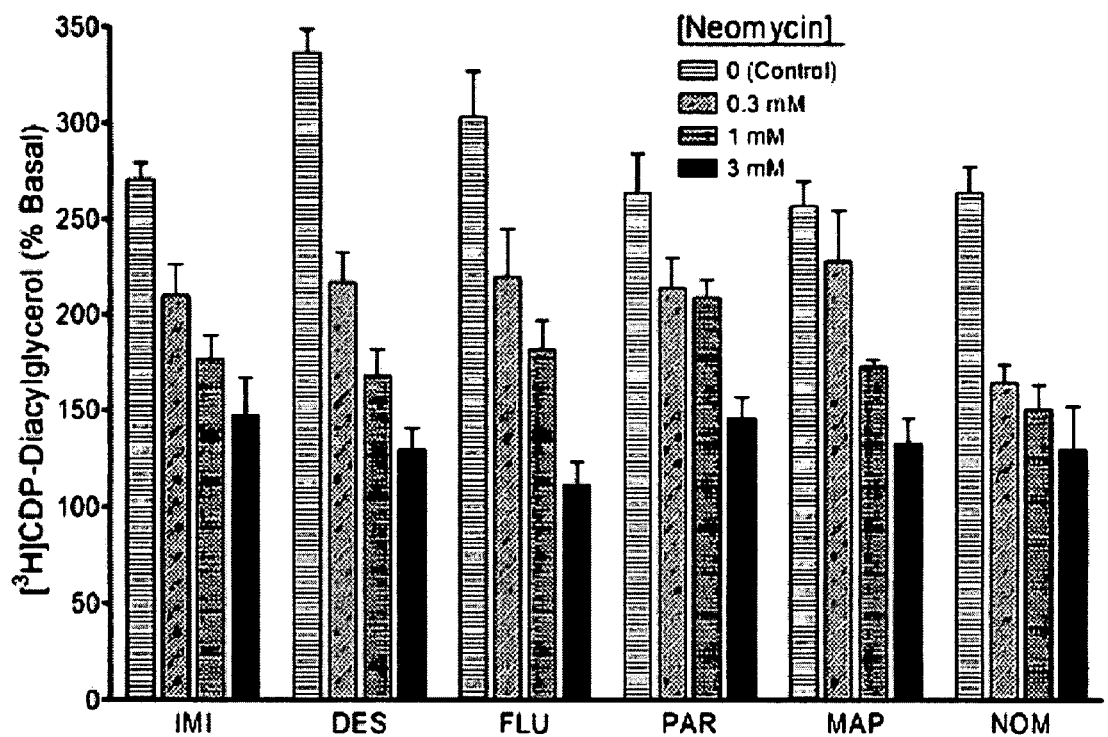
FIGS. 6A-6B demonstrate the inhibition of antidepressant-induced [$^3$H]CDP-diacylglycerol production and phosphoinositide synthesis by neomycin. Slices of rat prefrontal cortex or hippocampus prepared from the same rats were pre-labeled in parallel with [$^3$H]cytidine or [$^3$H]inositol and incubated with indicated concentrations of neomycin, followed by addition of 100 μM fluoxetine (FLU) or 300 μM imipramine (IMI), desipramine (DES), paroxetine (PAR), maprotiline (MAP), or nomifensine (NOM). Accumulated [$^3$H]CDP-diacylglycerol (FIG. 6A) or [$^3$H]phosphoinositides (FIG. 6B) were measured after 90 min. While only the hippocampus data are shown for CDP-diacylglycerol and the cortical data for phosphatidylinositides, each analyte was assessed in each brain region with similar results. Each bar is the mean±SEM (n=6). Neomycin significantly and concentration-dependently inhibited drug-induced [$^3$H]CDP-diacylglycerol production and [$^3$H]inositol phospholipid synthesis (ANOVA, $p<0.01$ for each drug). The effects of neomycin alone on CDP-diacylglycerol were not significant, whereas the 0.3 mM concentration was associated with a slight, but significant, increase in [$^3$H]phosphatidylinositide levels (Dunnett test, $*p<0.05$).
Figure 6B:
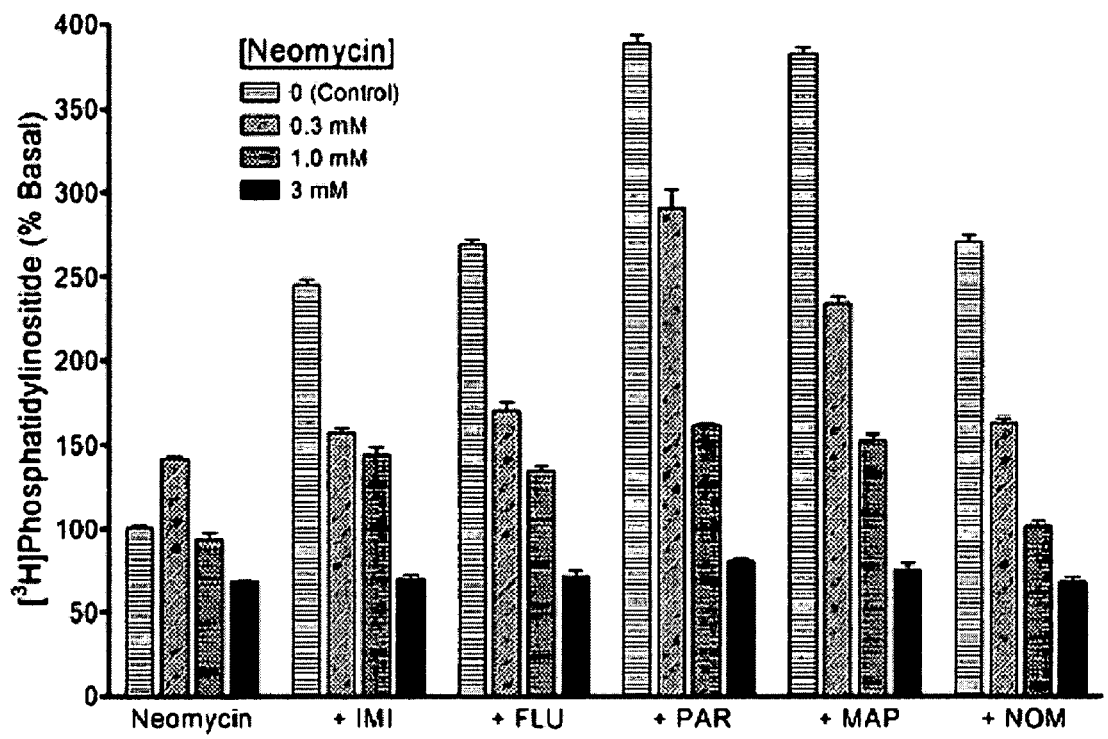

Antidepressant-Induced CDP-Diacylglycerol Formation Partially Depends on Phosphoinositide Hydrolysis Phosphoinositide hydrolysis is a major source, but not the only possible source, of diacylglycerol in the cell. To estimate the extent to which antidepressant-enhanced CDP-DG may derive from PI breakdown, PI hydrolysis was blocked and the consequent effects on the ability of antidepressant agents to induce CDP-DG accumulation were measured. First, the effects of the general PI metabolism inhibitor, neomycin, was tested against the maximally effective concentrations of the selected antidepressant agents. Neomycin concentration-dependently blocked the effects of imipramine, desipramine, fluoxetine, paroxetine, maprotiline, or nomifensine on CDP-DG production (FIG. 6A), PI resynthesis (FIG. 6B) or IP accumulation in hippocampal or prefrontal cortical brain slices. Increasing concentrations of neomycin produced complete blockade of both CDP-DG and PI responses.

Figure 7A:
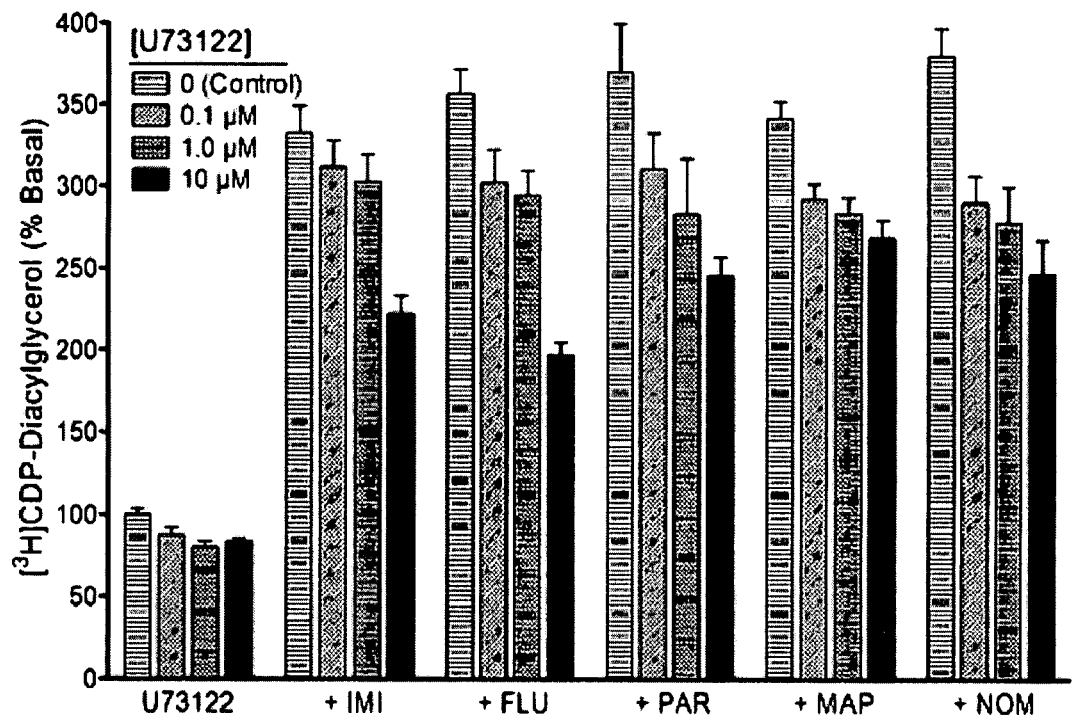
FIGS. 7A-7B demonstrate the effects of the PLC inhibitor U73122 on antidepressant-mediated CDP-diacylglycerol production and inositol phosphate accumulation. Cerebrocortical or hippocampal slices labeled with either [$^3$H]inositol or [$^3$H]cytidine were incubated in parallel with buffer alone or the indicated concentrations of U73122, followed by addition of 100 μM fluoxetine (FLU) or 300 μM imipramine (IMI), paroxetine (PAR), maprotiline (MAP), nomifensine (NOM), or SKF38393 (SKF) as indicated. Accumulated [$^3$H]CDP-diacylglycerol (FIG. 7A) or [$^3$H]inositol phosphates (FIG. 7B) were determined after 90 min. While only the hippocampus data are shown for inositol phosphates and the cortical data for CDP-diacylglycerol, each analyte was assessed in each brain region with similar results. Each bar is the mean±SEM (n=6). U73122 completely blocked [$^3$H]inositol phosphate accumulation stimulated by either antidepressant agent (ANOVA, $p<0.001$). Conversely, U73122 only partially reduced antidepressant drug-induced [$^3$H]CDP-diacylglycerol production. The phospholipase C inhibitor by itself showed no significant effect on either analyte.

Next, the effects of the selective PLC inhibitor, U73122, were tested on the drug responses. U73122 by itself did not significantly alter basal CDP-DG production (FIG. 7A) or IP accumulation (FIG. 7B), although a slight increase in IP was consistently noted. At concentrations ranging from 0.1 to 10 μM, U73122 significantly reduced, but was unable to completely block, antidepressant drug effects on CDP-DG production. Conversely, the PLC inhibitor completely blocked IP stimulation by 100 μM fluoxetine or 300 μM concentrations of imipramine, paroxetine, maprotiline, or nomifensine in hippocampal or cortical slices.

Figure 7B:
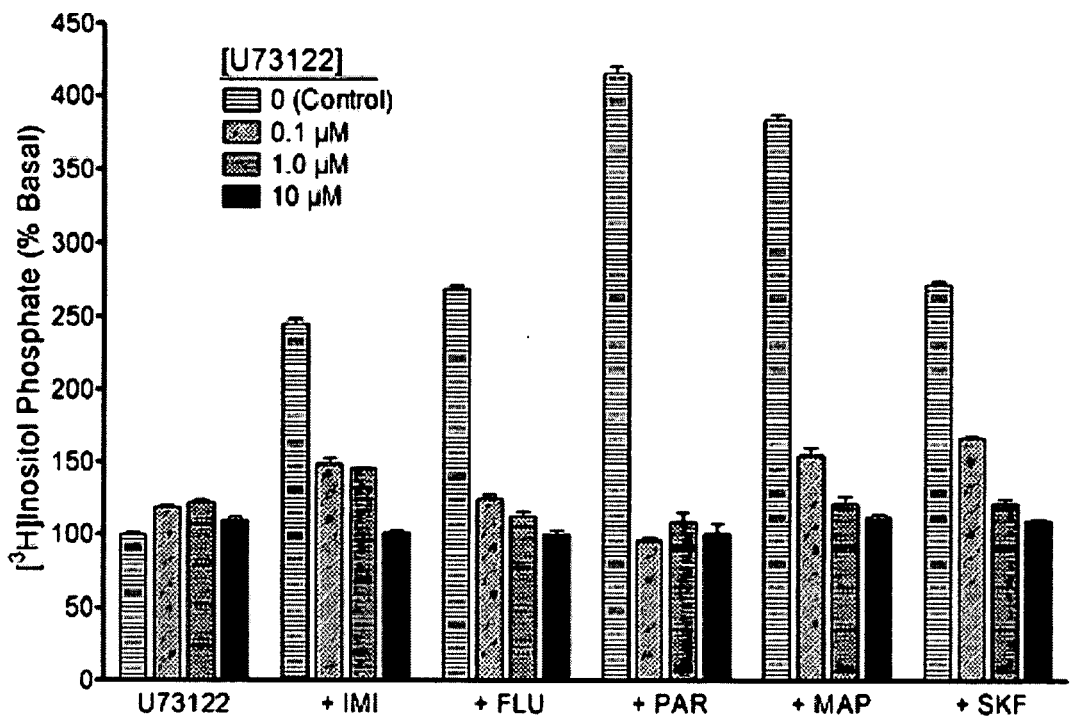

To validate the effects of U73122, the compound was tested against the action of SKF38393, a $D_1$ receptor agonist that is known to induce PI hydrolysis in these brain tissues (57,70). SKF38393-induced IP accumulation was blocked by U73122 with similar efficacies to the inhibition of the antidepressant responses (FIG. 7B). Moreover, U73123, an analog of U73122 that is ineffective in blocking PLC activity, was without effect on any of the CDP-DG or IP responses (data not shown). The effects of the SSRIs fluoxetine and paroxetine were more sensitive to inhibition by U73122 than the effects of the tricyclic agents.

Example 6

Lithium is not Required for Antidepressant Drug Effects on CDP-Diacylglycerol

Figure 8:
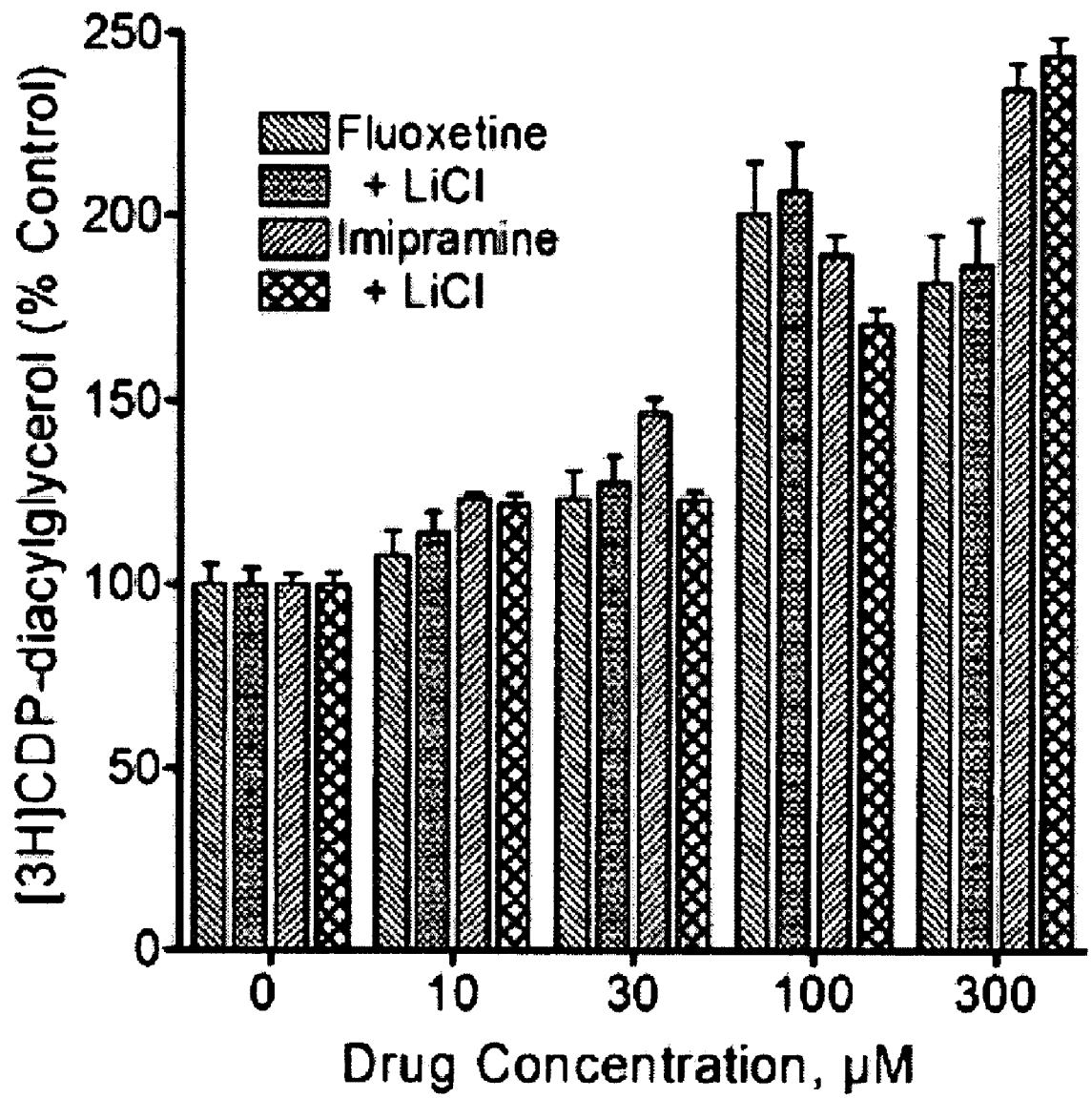
FIG. 8 demonstrates the effects of lithium chloride (LiCl) on antidepressant-induced [$^3$H]CDP-diacylglycerol production. Slices of prefrontal cortical or hippocampal tissues were labeled with [$^3$H]cytidine and incubated in the presence or absence of 5 mM LiCl. Indicated concentrations of fluoxetine or imipramine were added and, after 60 min, accumulated [$^3$H]CDP-diacylglycerol was measured. While the frontal cortex data are shown, similar observations were made in the hippocampus. Each bar is the mean±SEM (n=6). The presence of LiCl did not significantly alter the stimulatory effects of fluoxetine or imipramine on [$^3$H]CDP-diacylglycerol accumulation (ANOVA, $p>0.05$).

These experiments were designed to compare antidepressant drug effects on the IP and diacylglycerol arms of the inositol cycle. Thus, it was necessary to include LiCl in all test incubations. $Li^+$ is needed to block inositol monophosphatase and thereby enable the accumulation of released IPs to measurable levels. Selected antidepressant agents were tested for effects on CDP-DG in the absence or presence of 5 mM LiCl to determine if LI+ must be present to demonstrate antidepressant drug effects on CDP-DG. As shown in FIG. 8, LiCl did not significantly enhance or inhibit antidepressant drug-induced CDP-DG production, implying that the presence of $Li^+$ is not necessary to demonstrate the enhancing effects of antidepressant agents on CDP-DG production.

Example 7

Figure 9A:
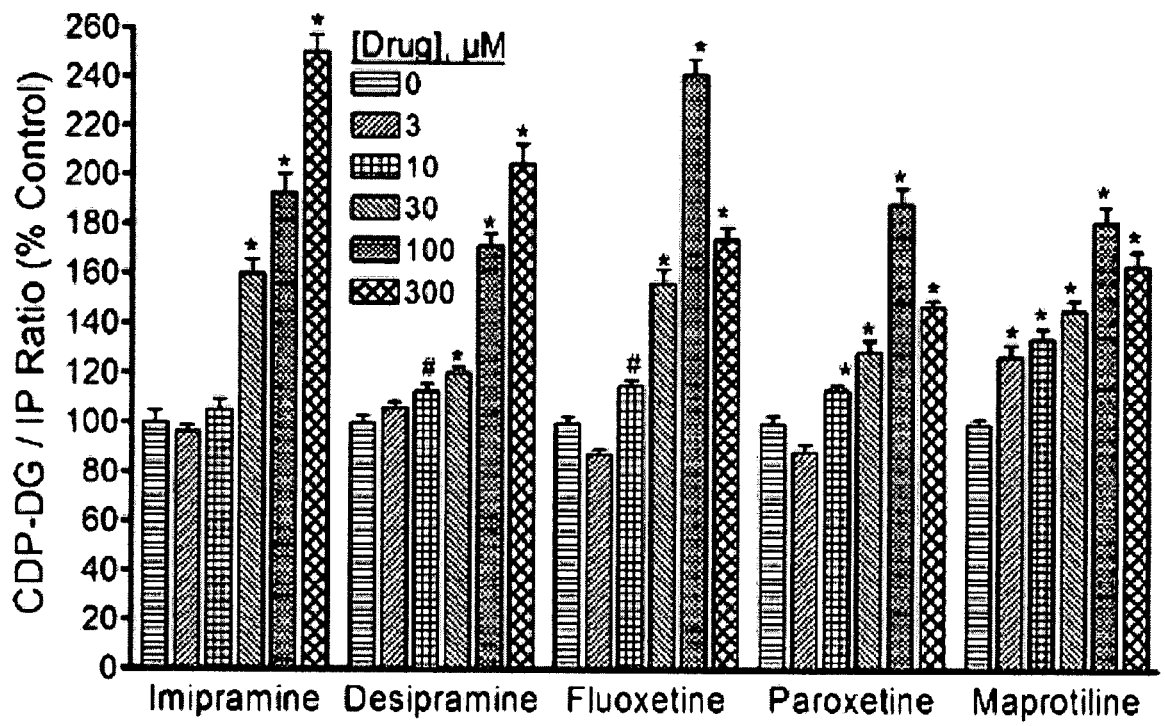
FIGS. 9A-9C are ratios of antidepressant-induced CDP-diacylglycerol versus inositol phosphates. The data in FIGS. 1A-1C, 2A-2B, 3A-3C, 4A-4B, and 5A-5C were recalculated by dividing the CDP-diacylglycerol effects of each concentration of each antidepressant agent by the corresponding effects of the agent on inositol phosphate accumulation to yield the CDP-diacylglycerol/inositol phosphate (CDP-DG/IP) ratios shown. To facilitate merging of data from multiple experiments, these values were converted to percentages relative to the ratio values in the respective control samples and then averaged to give the mean±SEM shown for the classic agents (FIG. 9A), phenelzine (FIG. 9B), and hydralazine (FIG. 9C). Data for the hippocampus are shown, but similar observations were made in the cortical tissues. Data for each agent were analyzed by One-Way ANOVA followed by posthoc Dunnett tests. $^#p<0.05$; $*p<0.01$; compared to the respective control (zero drug concentration).
Figure 9B:
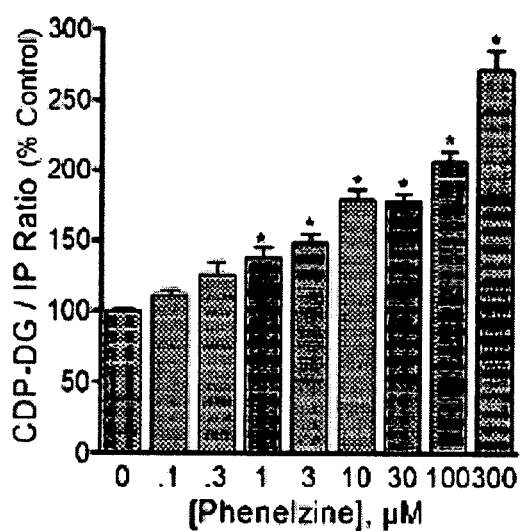
Figure 9C:
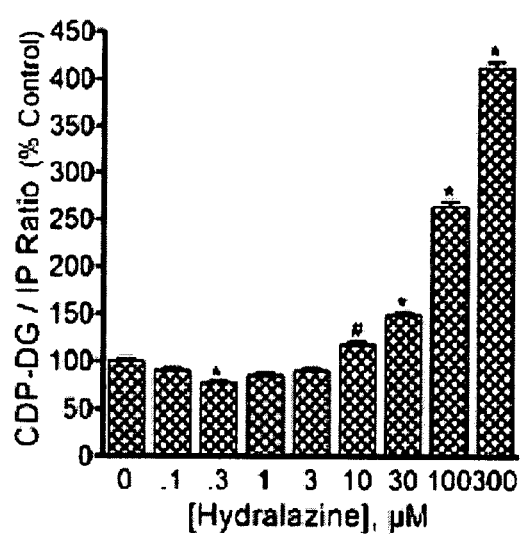

Antidepressants Elicit Relatively Greater Stimulation of CDP-Diacylglycerol Production than IP Formation To determine if antidepressant agents exert differential effects on CDP-DG production compared to PI hydrolysis, the ratios of CDP-DG production relative to the IPs (CDP-DG/IP ratio) in corresponding treatment conditions were examined. The ratios were calculated from the data in FIGS. 1A-1C, 2A-2B, 3A-3C, 4A-4B, and 5A-5C and the results are shown in FIGS. 9A-9C. With each antidepressant agent, the CDP-DG/IP ratios increased significantly with increasing drug concentrations. This was true for different classes of drugs, including the MAOIs phenelzine and hydralazine.

Example 8

Monoamine Receptor Agonists Exert Divergent Effects on CDP-Diacylglycerol

Figure 10A:
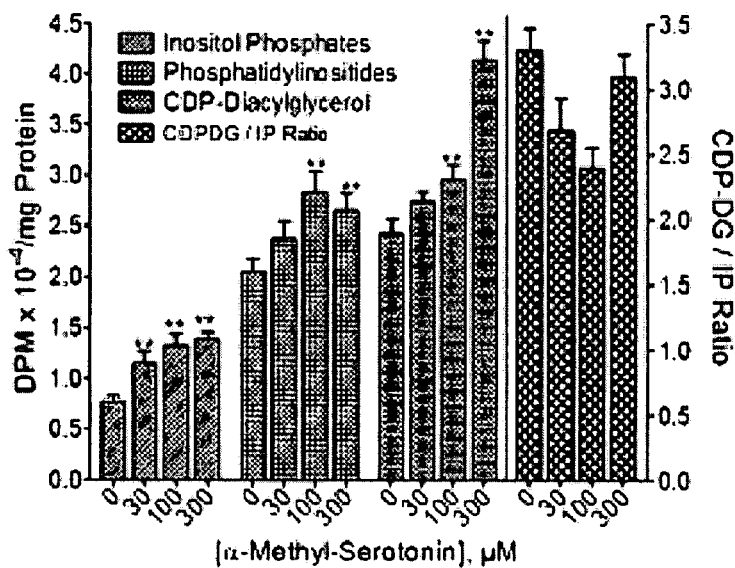
FIGS. 10A-10C demonstrate the effects of α-methylserotonin, carbachol, and phenylephrine on CDP-diacylglycerol production, inositol phosphate accumulation and phosphatidylinositide synthesis. Slices of prefrontal cortical or hippocampal tissues were pre-labeled with [$^3$H]cytidine or [$^3$H]inositol in parallel and then incubated in the presence of 5 mM LiCl. Indicated concentrations of the agonists α-methylserotonin (FIG. 10A), carbachol (FIG. 10B) and phenylephrine (FIG. 10C) were added for 90 min, followed by assay of the levels of [$^3$H]CDP-diacylglycerol, [$^3$H]inositol phosphates, and [$^3$H]phosphoinositides. Calculated ratios of CDP-diacylglycerol over inositol phosphates (CDP-DG/IP ratios) are depicted at the far right relative to the scale on the right y-axis. Each bar is the mean±SEM (n=15 for α-methylserotonin, 12 for carbachol, 9 for phenylephrine). Data were separately analyzed by One-Way ANOVA for each receptor agonist. $*p<0.05$; $**p<0.01$, Dunnett test compared to the respective control (zero drug concentration).
Figure 10B:
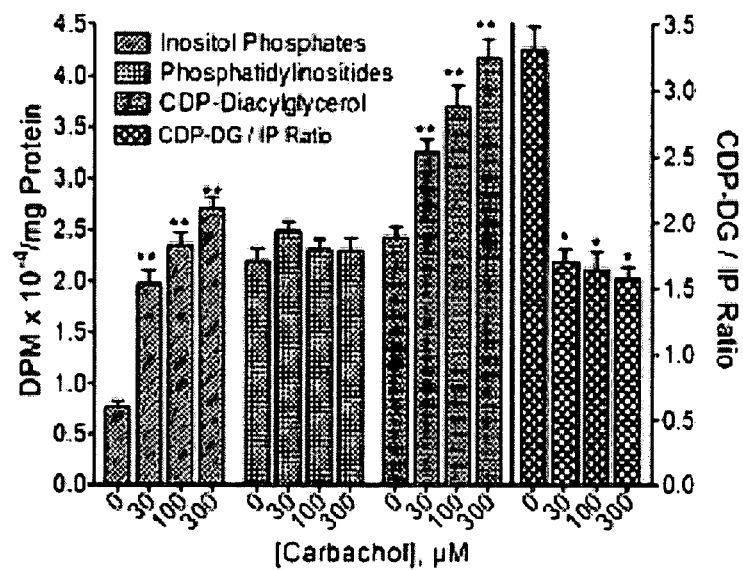
Figure 10C:
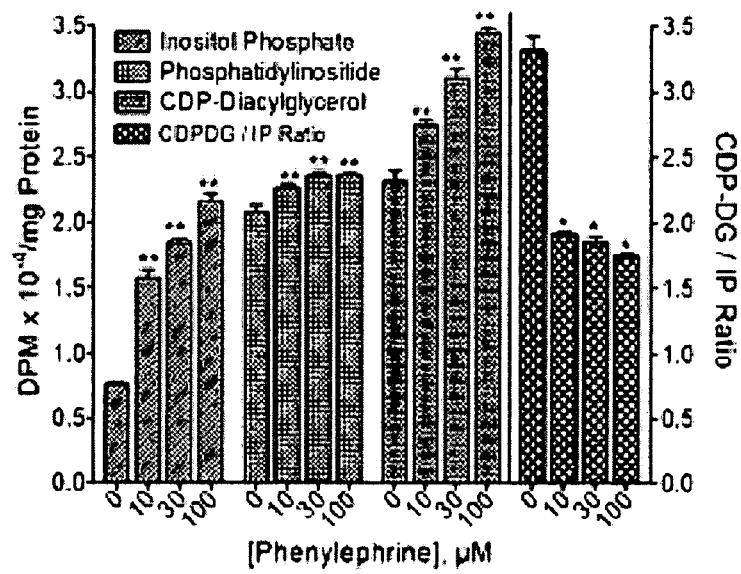
Figure 11A:
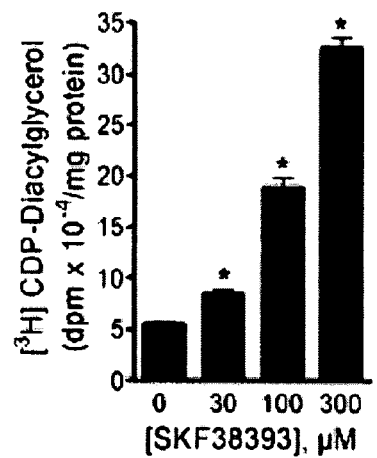
FIGS. 11A-11F demonstrate the effects of SKF38393 on CDP-diacylglycerol production, inositol phosphate accumulation and phosphatidylinositide synthesis. Prefrontal cortical slices pre-labeled with [$^3$H]cytidine or [$^3$H]inositol in parallel were incubated with indicated concentrations of SKF38393 in the presence of 5 mM LiCl for 90 min, followed by assay of [$^3$H]CDP-diacylglycerol (FIG. 11A), [$^3$H]phosphoinositides (FIG. 11B) and [$^3$H]inositol phosphates (FIG. 11C). Calculated ratios of CDP-diacylglycerol over inositol phosphates (CDP-DG/IP ratio) (FIG. 11D), phosphatidylinositides (CDP-DG/PI ratio) (FIG. 11E), or the sum of the inositol phosphates and phosphatidylinositides (CDP-DG/IPPI ratio) (FIG. 11F) are shown. Each bar is the mean±SEM (n=12). Data were analyzed by One-Way ANOVA and posthoc Dunnett tests. $*p<0.05$; $**p<0.01$, compared to the respective control.
Figure 11B:
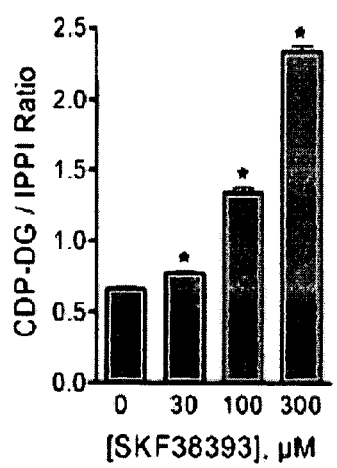
Figure 11C:
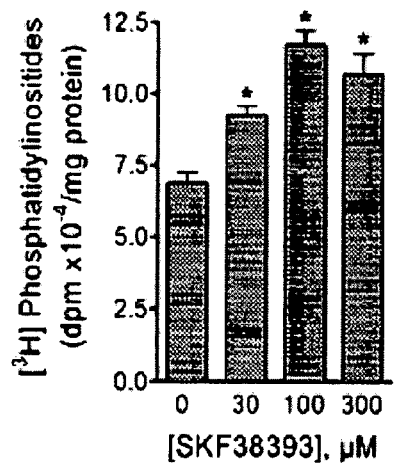
Figure 11D:
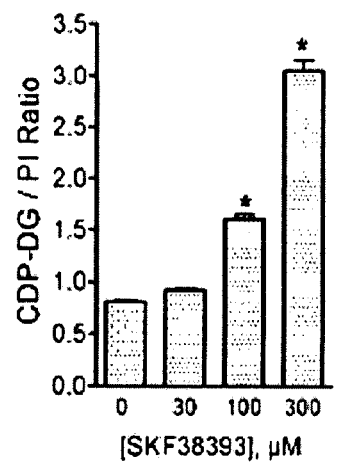
Figure 11E:
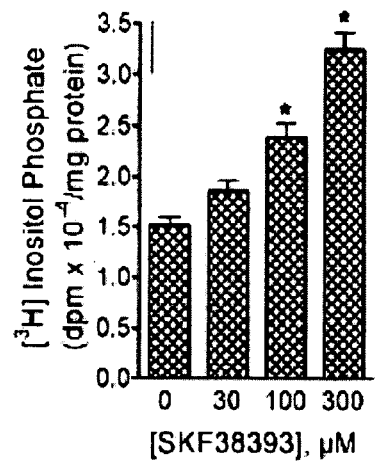
Figure 11F:
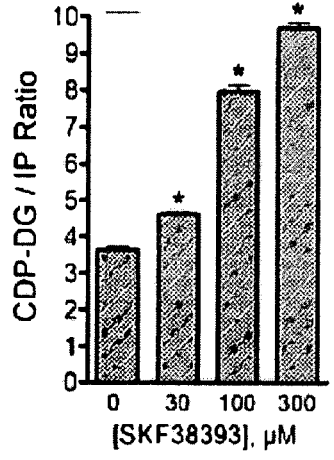
Figure 12A:
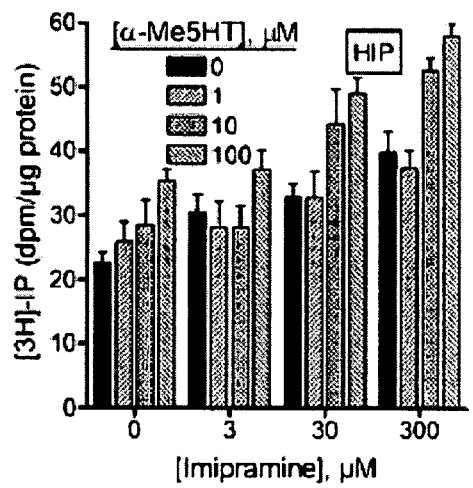
FIGS. 12A-12R demonstrate the effects of preincubation with representative antidepressant agents on α-methylserotonin-induced [$^3$H]IP accumulation in rat hippocampus (FIGS. 12A-12F), the prefrontal cortex (FIGS. 12G-12L) and striatal tissue (FIGS. 12M-12R). Tissue slices were labeled with [$^3$H]inositol for 60 min in the absence or the presence of indicated concentrations of imipramine, desipramine, fluoxetine, paroxetine, and maprotiline. Tissues were washed, distributed into fresh tubes and incubated at 37° C. in the presence of 5 mM LiCl. Indicated concentrations of the 5HT$_2$ agonist, α-methylserotonin (α-Me5HT), were added and were allowed to act for 60 min, after which the tissue content of inositol phosphates (IP, viz., IP$_1$+IP$_2$+IP3) was determined. Each bar is the mean±SEM (N=6–9). Data for each drug were separately analyzed by Two-Way ANOVA of IP response by drug concentration by α-Me5HT concentration; this was followed with 20 posthoc Dunnett tests to detect the minimal concentration of test drug that significantly enhanced the dose-related effects of α-Me5HT.
Figure 12B:
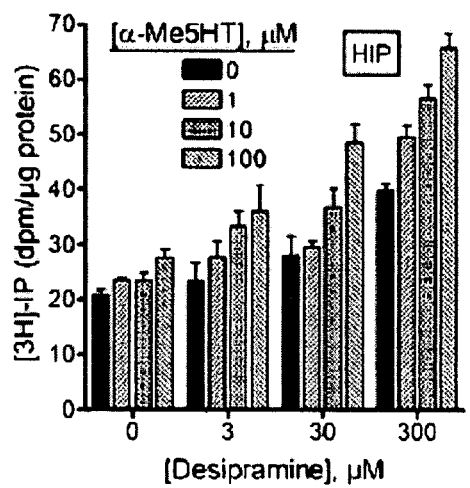
Figure 12C:
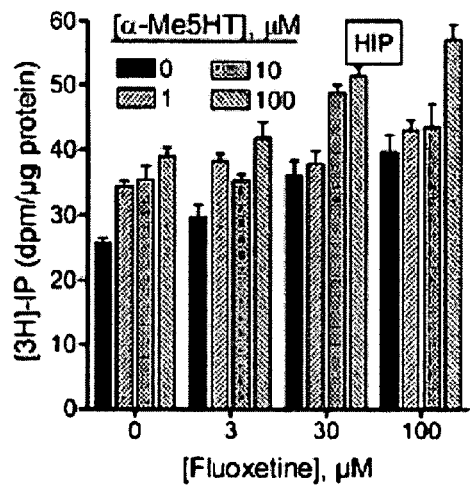
Figure 12D:
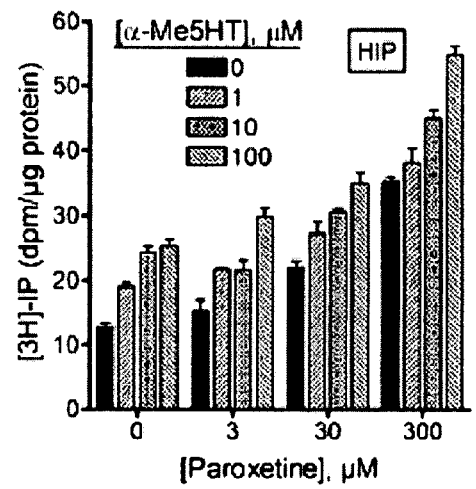
Figure 12E:
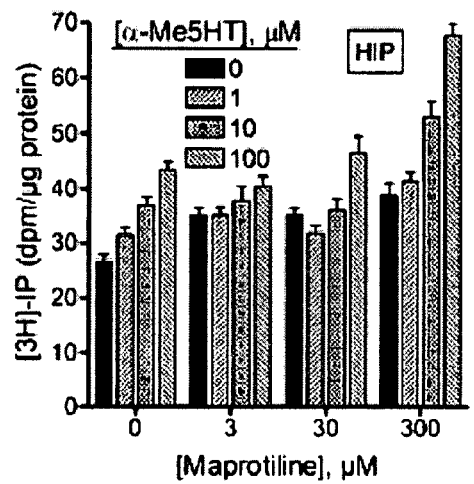
Figure 12F:
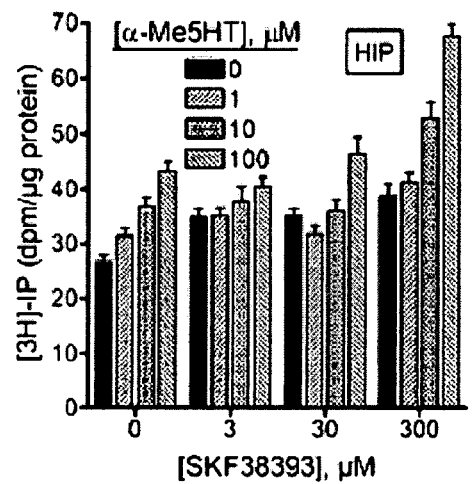
Figure 12G:
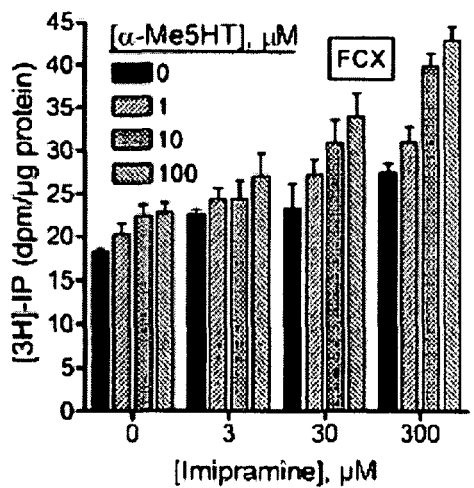
Figure 12H:
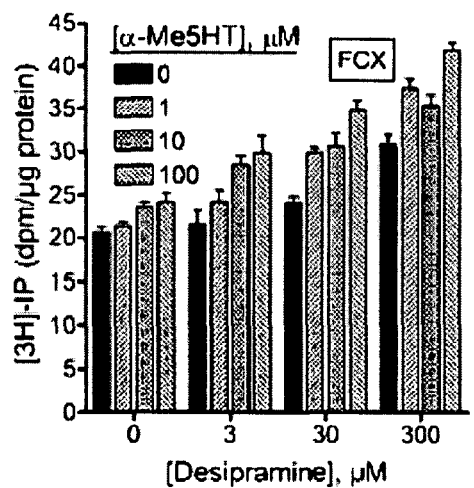
Figure 12I:
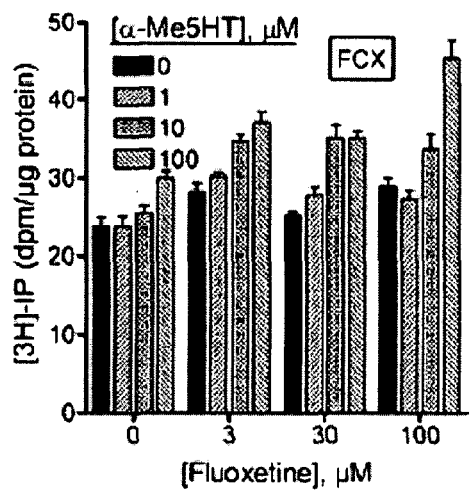
Figure 12J:
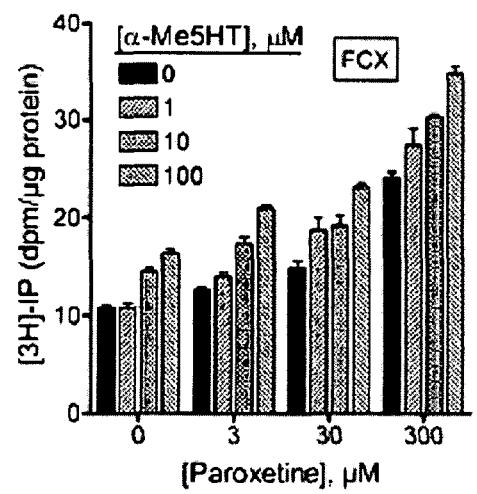
Figure 12K:
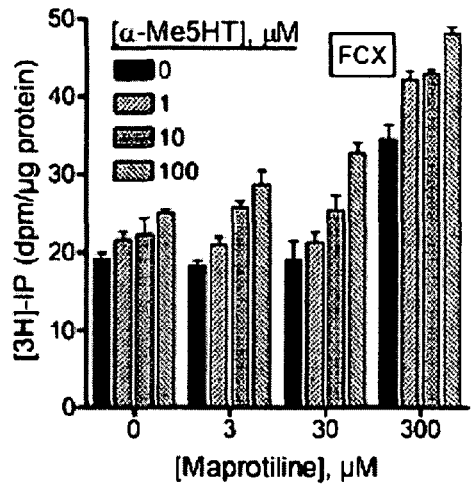
Figure 12L:
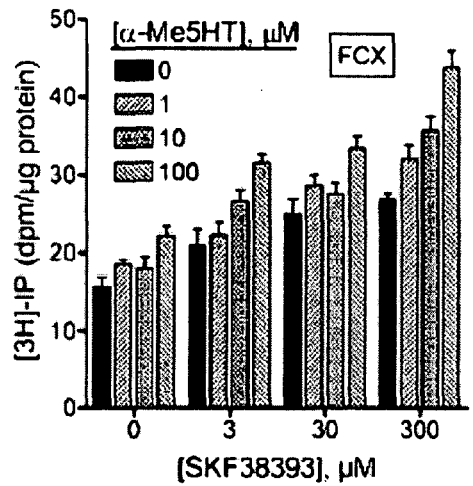
Figure 12M:
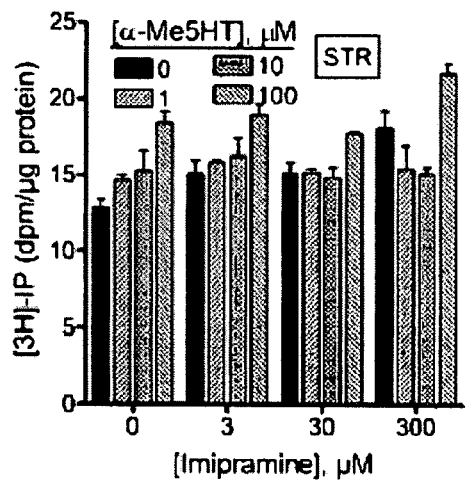
Figure 12N:
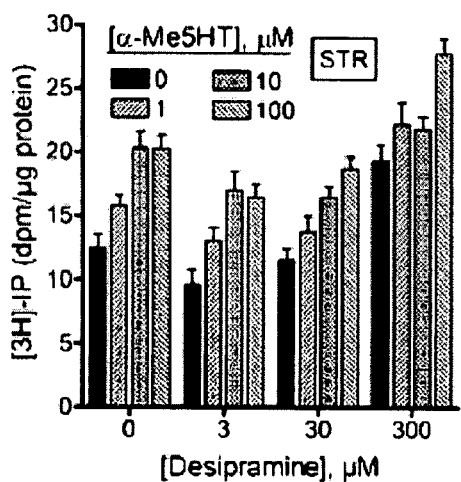
Figure 12O:
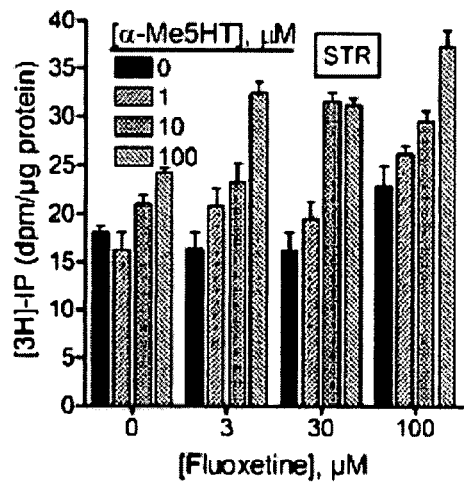
Figure 12P:
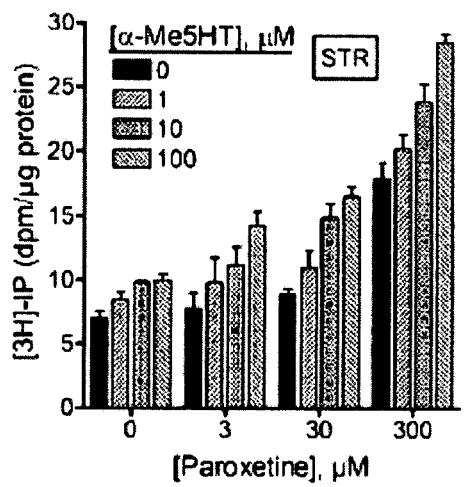
Figure 12Q:
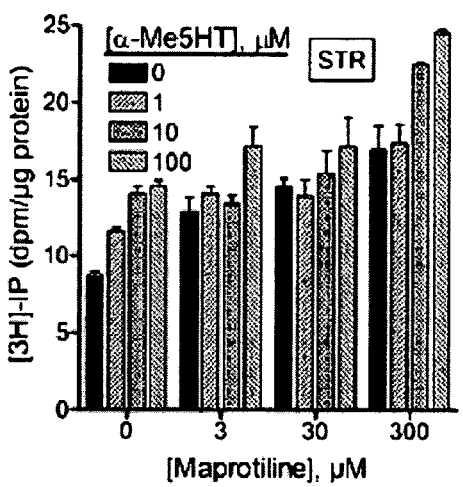
Figure 12R:
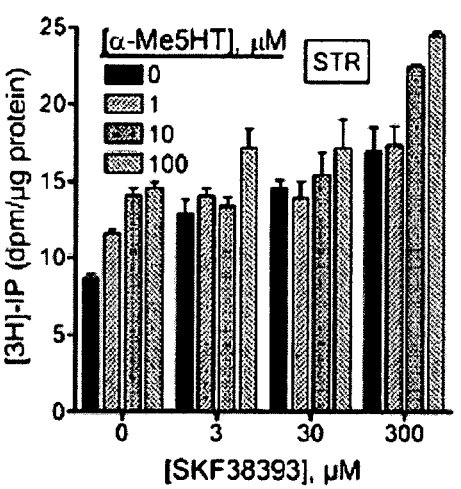

To determine which, if any, of the endogenous monoaminergic systems may show similar profiles of CDP-DG/IP effects, agonists that act directly at PLC-coupled monoaminergic receptors: α-methylserotonin ($5HT_2$ serotonergic), carbachol (muscarinic cholinergic), SKF38393 ($D_1$-like dopaminergic), and phenylephrine (alpha-adrenergic) were used. Corresponding CDP-DG ratios were calculated as for the antidepressant agents. As shown, α-methylserotonin, carbachol, phenylephrine (FIGS. 10A-10C) or SKF38393 (FIGS. 11A-11D) significantly increased IP accumulation and CDP-DG production in frontal cortex or hippocampal tissues. Carbachol failed to increase PI synthesis, SKF38393 significantly enhanced PI synthesis, while the other two agents had significant but relatively small effects on PI. The ratios of CDP-DG production relative to IP accumulation are shown on the far right of the graphs in FIGS. 10A-10C and FIGS. 11A-11D.

With both carbachol and phenylephrine, there was a dramatic decrease in the CDP-DG/IP ratio. While the ratio did not decrease as much for α-methylserotonin, there was no concentration-related increase either. Conversely, SKF38393 increased CDP-DG/IP ratios significantly and in a manner similar to the antidepressants (FIGS. 11A-11D). Indeed, even the ratios of CDP-DG relative to PIs or the combination of both inositol derivatives (CDP-DG/IP&PI) were significantly enhanced. Thus, agonists at the direct PLC-coupled monoamine receptors showed parallel and corresponding changes between CDP-DG and the inositides, except for the dopamine agonist which, like the antidepressants, induced proportionately greater production of CDP-DG relative to inositide derivatives.

Example 9

Antidepressants Enhance Methylserotonin-Stimulated IP Accumulation in [$^3$H]inositol-Prelabeled Tissues Brain hippocampal, frontal cortical, and striatal slices were labeled with [$^3$H]inositol in the presence of various concentrations of selected antidepressant agents and, after washing the tissues, aliquots of the slices were incubated with indicated concentrations of α-methylserotonin for an additional 60 min. The levels of accumulated [$^3$H]IPs, assayed by Dowex ion exchange chromatography, are shown for the hippocampus (FIGS. 12A-12F), frontal cortex (FIGS. 12G-12L) and striatum (FIGS. 12M-12R). By itself, α-Me5HT induced significant increases in IP accumulation; these effects, however, were significantly enhanced in tissues that had been prelabeled with tritiated inositol in the presence of the antidepressant agent imipramine, desipramine, fluoxetine paroxetine, and maprotiline.

The effects of α-methylserotonin were further concentration-dependently enhanced in hippocampal tissues that were prelabeled in the presence of each antidepressant agent ($p<0.001$), in frontal cortex tissues prelabeled in the presence of imipramine and desipramine ($p<0.02$) and the other agents ($p<0.001$ each), and in striatal tissues prelabeled in the presence of fluoxetine, paroxetine, and maprotiline ($p<0.001$). α-Methylserotonin effects, however, were not significantly enhanced in striatal tissues prelabeled in the presence of imipramine or desipramine ($p>0.05$). In all tissues where there were significant effects of antidepressant agents, there were significant interactions between the concentrations of antidepressant agent used and the concentrations of the $5HT_2$ agonist tested. Hence, the concentration-related effects of α-methylserotonin were maintained, but accentuated, in tissues prelabeled under the influence of the antidepressant agents.

The zero α-methylserotonin data represent tissues that had been prelabeled in the presence of the indicated concentrations of antidepressant agents, further incubated alongside the α-methylserotonin-tested tissues, and subsequently analyzed for the basal content of inositol phosphates. In these tissues that did not receive α-methylserotonin, there were generally increased levels of IPs with increasing concentrations of the antidepressant agents.

Thus, mere prelabeling of the tissues in the presence of antidepressant agents led to increased accumulations of inositol phosphates even in the absence of exogenous $5HT_2$ receptor stimulation. These effects were statistically significant for all agents at least their highest tested concentrations in each brain region (ANOVA, $p<0.001$ in each case). The net effects of the combined exposure to antidepressant and α-methylserotonin were not significantly different from the sum of the separate effects of antidepressant and α-methylserotonin, thus suggesting an additive mechanism of interaction between AD and α-methylserotonin treatments.

Example 10

Effects of $5HT_2$ Receptor Blockade on Drug-Induced IP Accumulation

Figure 13A:
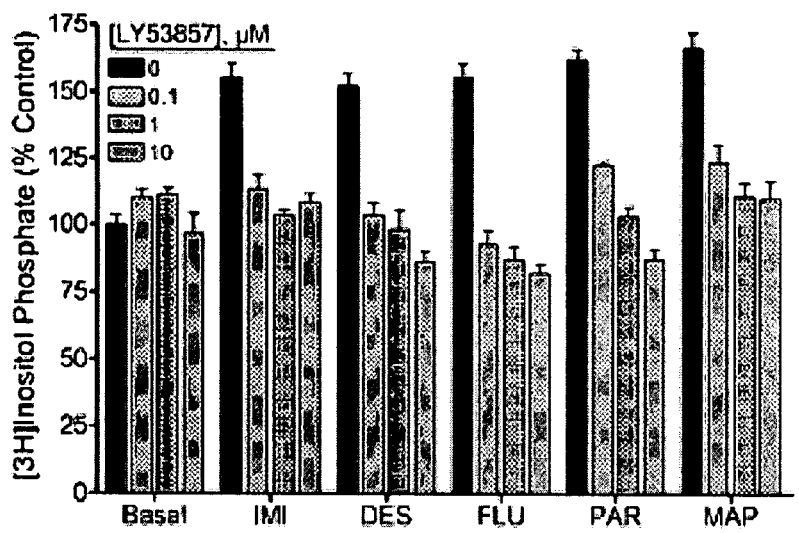
FIGS. 13A-13C demonstrate the effects of the selective 5HT$_2$ receptor antagonist, LY53857, on antidepressant drug action. Hippocampal slices were incubated with either [$^3$H] inositol (FIGS. 13A-13B) or [$^3$H]cytidine (FIG. 13C) for 30 min, followed by addition of indicated concentrations of LY53857 (6-methyl-1-(1-methylethyl)-ergoline-8β-carboxylic acid 2-hydroxy-1-methylpropyl ester maleate). This was followed after 15 min by addition of buffer alone (Basal) or 300 μM imipramine (IMI), desipramine (DES), paroxetine (PAR), or maprotiline (MAP), or 100 μM fluoxetine (FLU). After 60 min, tritiated inositol phosphate, inositol phospholipids, or CDP-diacylglycerol were assayed. Each bar is the mean±SEM (n=6). Data for each analyte were normalized across experiments and test drugs and then were analyzed for each drug by One-Way ANOVA of responses measured at the four concentration conditions of LY53857 (0, 0.1, 1, 10 μM). The ANOVAs were followed with Dunnett tests comparing the response in the presence of each concentration of LY53857 to the control effect of the antidepressant alone.
Figure 13B:
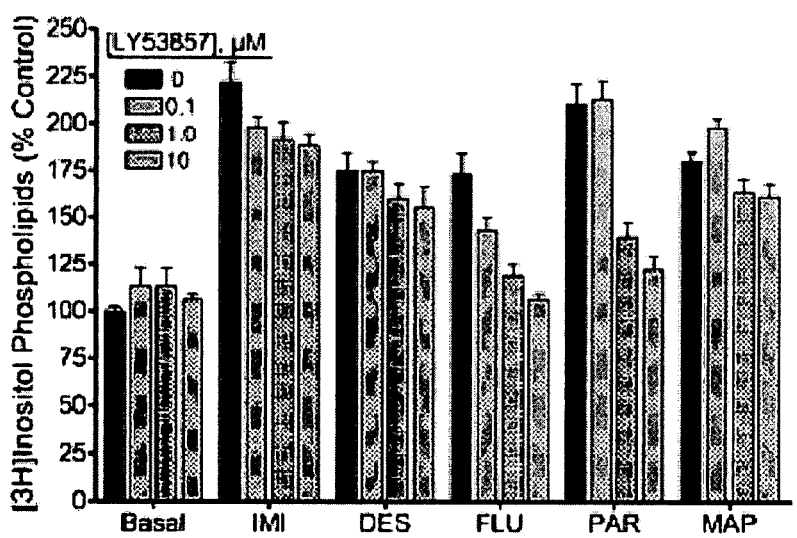
Figure 13C:
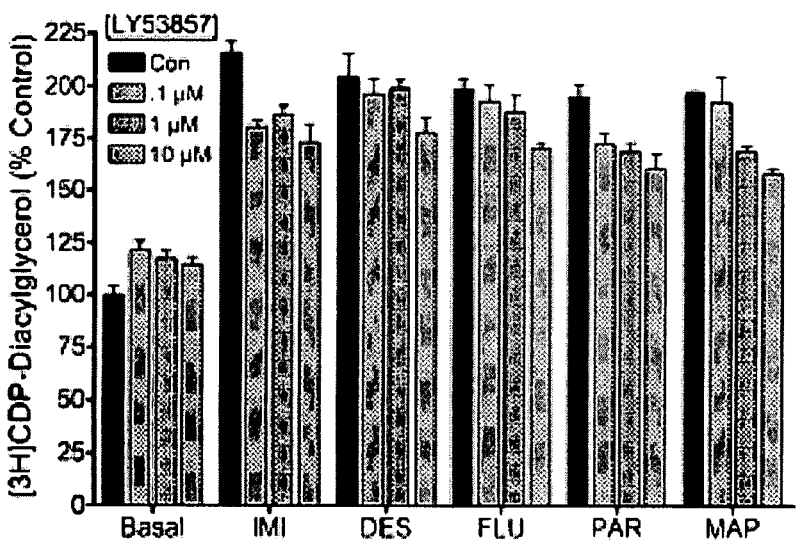

To examine the extent to which the enhancing effects of antidepressant agents on inositol phosphate accumulation were dependent on postsynaptic $5HT_2$ receptor stimulation, each antidepressant was challenged with a range of concentrations of the $5HT_2$ receptor-selective antagonist, LY53857 (71-72). The antagonist was added after the prelabeling phase, but 15 min prior to the addition of α-methylserotonin to the incubating slices. LY53857 did not significantly alter the basal levels of IPs or PIs, but increased CDP-diacylglycerol by 20% at the 0.1 µM concentration (FIGS. 13A-13C). The $5HT_2$ antagonist completely blocked the IP responses to each of the AD agents ($p<0.001$ in each case). PI labeling and CDP-diacylglycerol responses were statistically significantly inhibited ($p<0.05$ or better) for all drugs; however, only the inhibition of PI labeling induced by fluoxetine and paroxetine was substantial.

While the results shown are for the hippocampus, similar observations were made in frontal cortex tissues. With regard to antidepressant-enhanced phosphatidylinositol resynthesis, $5HT_2$ receptor blockade significantly inhibited the effects of the SSRIs fluoxetine and paroxetine, but the effects of the tricyclic agents imipramine and desipramine or those of maprotiline were only partially, though significantly, reduced. Moreover, antidepressant drug effects on CDP-diacylglycerol were only minimally, though statistically significantly, inhibited by the $5HT_2$ antagonist. Thus, antidepressant-facilitated release of IP second messengers requires intact $5HT_2$ receptor function, whereas antidepressant drug effects on CDP-diacylglycerol or phosphatidylinositol labeling may facilitate, but not depend on, postsynaptic $5HT_2$ receptor signaling.

Example 11

Figure 14:
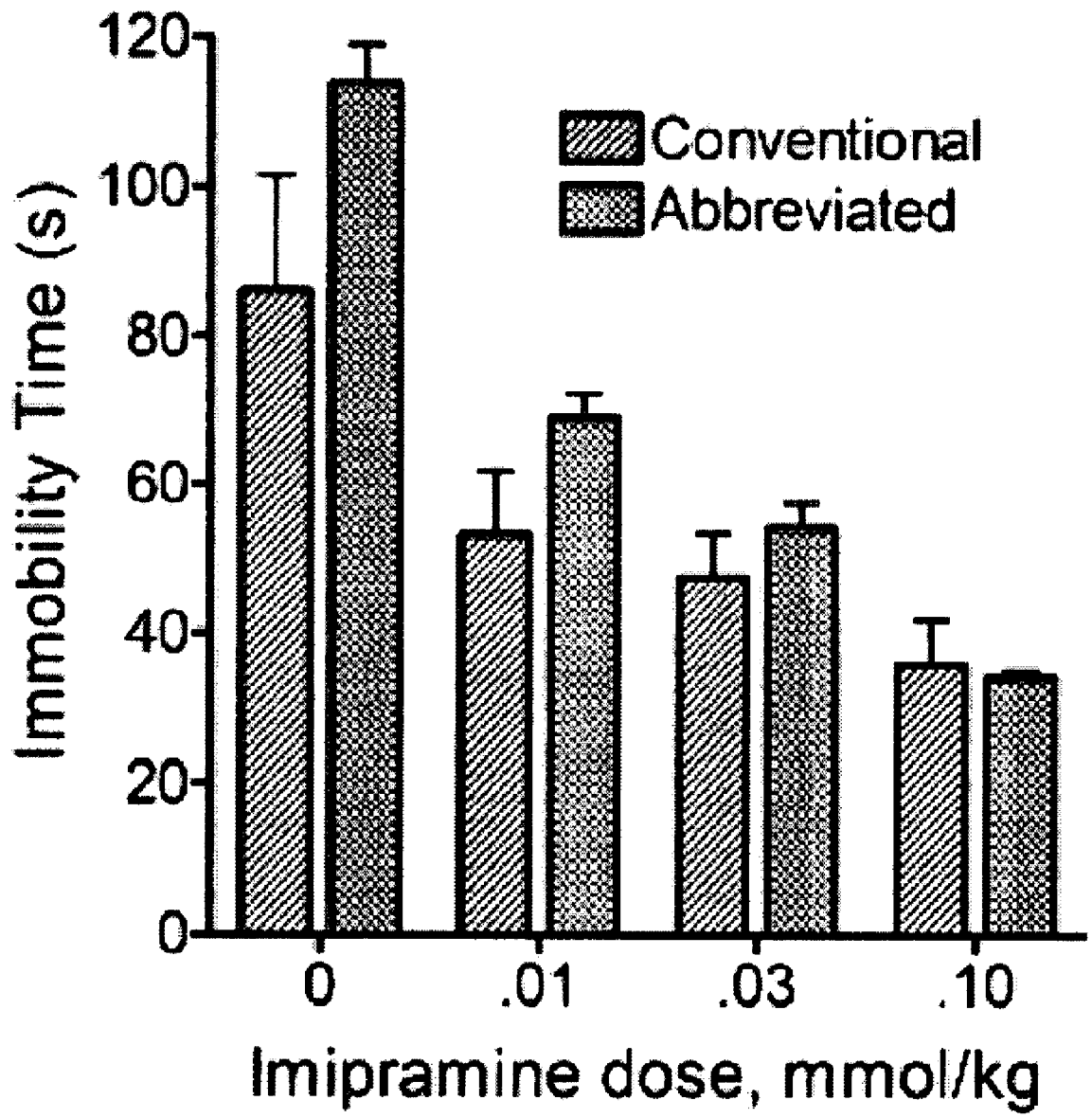
FIG. 14 is a comparison of Imipramine effects in the forced swim test conducted by the conventional and modified regimens. One group of rats was acclimated once in the swim chamber and subgroups of three animals each were administered indicated doses (corresponding to 0, 3, 10, and 30 mg/kg) of imipramine at 24, 3, and 1 h before behavioral testing (conventional regimen). The other group of rats from the same batch was acclimated twice at 48 and 24 h before the time of testing and subgroups were administered the same doses of imipramine at 3 and 1 h before behavioral testing. Animals in each group were then tested in the forced swim apparatus for 5 min and the immobility times determined. The mean coefficient of variance for each dataset was 2.9 for the conventional regimen and 1.1 for the modified regimen. Each bar is the mean±SEM (n=6). Each regimen produced significant and dose-related imipramine effects ($p<0.001$ each).
Figure 15A:
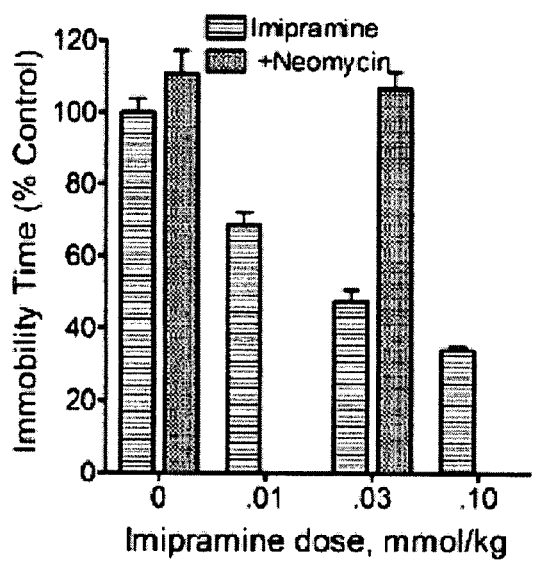
FIGS. 15A-15D demonstrate the effects of neomycin on antidepressant drug responses in the forced swim test. Animals were prepared as in FIG. 14 for the modified regimen. Neomycin was administered by iv injection through the tail vein 2 h prior to behavioral testing. Test drugs were administered at indicated doses 3 and 1 h before behavioral testing. The graphs show combined data from using one of imipramine (FIG. 15A), fluoxetine (FIG. 15B), maprotiline (FIG. 15C), and SKF38393 (FIG. 15D) and neomycin. Each antidepressant agent was examined for dose-dependent effects (n=6 per data point) and the effects of neomycin on a selected dose point of the antidepressant drug (n=8). Immobility response data for set one were analyzed by one-way ANOVA (response by dose) in order to determine if the drug by itself produced significant effects. Data for set two were analyzed by one-way ANOVA (response by group, where group comprised control, neomycin, drug, neomycin+drug), followed by posthoc Tukey tests. Each test drug produced significant reductions in immobility times ($p<0.01$ each compared to control). Neomycin alone did not significantly alter immobility response compared to saline-treated control. Neomycin pretreatment abolished the immobility-reducing effects of each tested antidepressant drug ($p<0.001$ comparing neomycin+antidepressant to antidepressant alone).
Figure 15B:
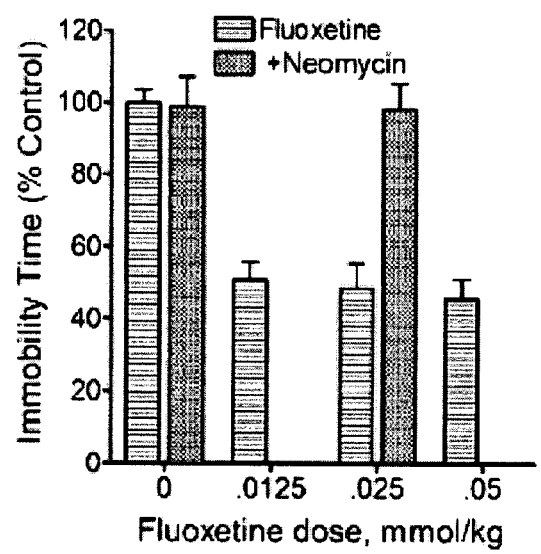
Figure 15C:
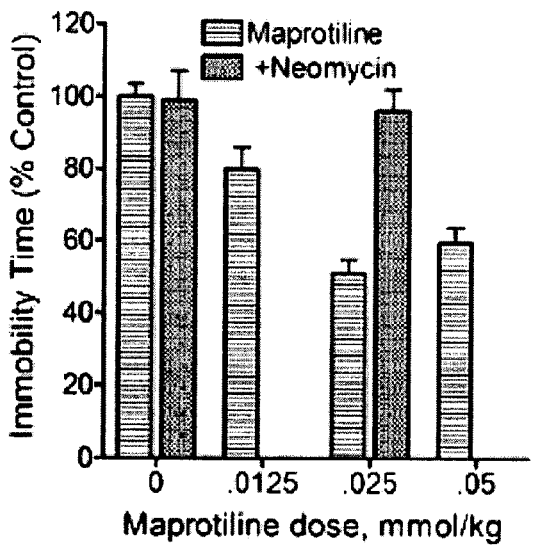
Figure 15D:
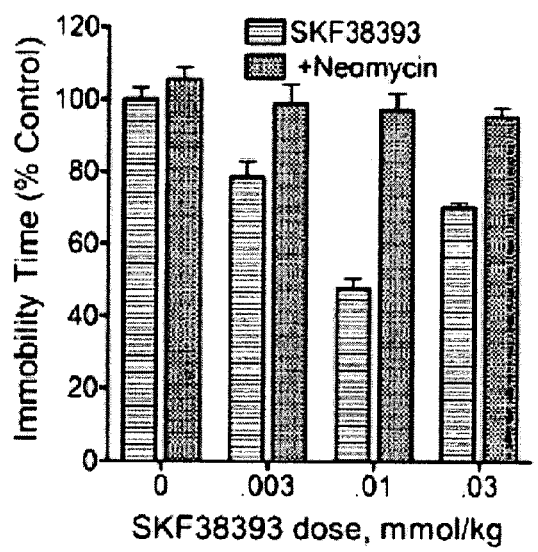

Effects of Blocking Endogenous PI Metabolism on Antidepressant-Induced Behavioral Effects in the Forced Swim Test Imipramine was first tested by both the conventional regimen using one acclimation with three-point drug administration and the current modification using two acclimations with two-point drug administration, of the forced swim test. As shown in FIG. 14, either method produced significant dose-related effects for imipramine on immobility behavior ($p<0.001$ for each dataset). Immobility times were slightly higher in the modified test than in the conventional test ($p<0.05$). Most significantly, the variability in the data was much reduced in animals that underwent two acclimation sessions; hence, the mean coefficient of variation was 2.6-fold lower in the modified test than in the conventional approach.

Following pretreatment with saline (controls) or neomycin, animals were subjected to the forced swim test in the presence or absence of selected antidepressant agents (FIGS. 15A-15D). Imipramine, fluoxetine, and maprotiline each induced significant and dose-dependent reductions of immobility times in the forced swim test, and these effects were completely reversed in animals that received neomycin pre-treatments. Yet, neomycin by itself did not significantly alter basal immobility times in any of the experiments. SKF38393 was tested in the absence and presence of neomycin. SKF38393 significantly decreased immobility times similar to the effects of the clinical antidepressant agents and this action was blocked by neomycin. Apparently, the acute behavioral effects of the drugs in at least the forced swim test depend on intact functioning of brain PI systems.

The following references are cited herein:
1. Waslick et al. (2002). In: Shaffer D, Waslick B D, (eds). The many faces of depression in children and adolescents. American Psychiatric Publishing, Inc.: Washington D.C. pp 1-29.
2. Costello et al. (2003). Arch Gen Psychiatry 60:837-844.
3. Hasin et al. (2005). Arch Gen Psychiatry 62:1097-1106.
4. Ciraulo et al. (2004). Clinical pharmacology and therapeutics of antidepressants. In: Ciraulo D A, Shader R I, (eds). Pharmacotherapy of depression. Humana Press: Totowa N.J. pp 33-119.
5. Taylor et al. (2005). Cell Signal 17:549-557.
6. Feighner J P (1999). J Clin Psychiatry 60:4-11.
7. Frazer A (2000). J Clin Psychiatry 61:25-30.
8. Gould T D, Manji H K (2002). J Psychosom Res 53:687-697.
9. Delgado P L (2004). J Clin Psychiatry 65:25-30.
10. De Vivo M, Maayani S (1986). J Pharmacol Exp Ther 238:248-253.
11. De Vivo M, Maayani S (1990). Biochem Pharmacol 40:1551-1558.
12. Dumuis et al. (1988). Mol Pharmacol 33:178-186.
13. Undie et al. (1994). J Neurochem 62:2045-2048.
14. Dwivedi et al. (2002). Neuropharmacology 43:1269-1279.
15. Fumagalli et al. (2005). J Neurochem 93:1551-1560.
16. Chen J, Rasenick M M (1995). J Pharmacol Exp Ther 275:509-517.
17. Hines L M, Tabakoff B (2005). Biol Psychiatry 58:955-962.
18. Odagaki et al. (2001). Brain Res 898:224-231.
19. Shimizu et al. (1996). J Pharmacol Exp Ther 279:1551-1558.
20. Qu et al. (2003). npp 28:1219-1226.
21. Nibuya et al. (1996). J Neurosci 16:2365-2372.
22. Yamada et al. (2003). J Neural Transm 110:671-680.
23. Butler P D, Barkai A I (1987). Adv Exp Med Biol 221:531-547.
24. Pandey et al. (1991a). Psychopharmacol Bull 27:255-261.
25. Fukuda et al. (1994). Neurochem Int 25:567-571.
26. Pacheco et al. (1996). Brain Res 723:37-45.
27. Pandey et al. (1991b). J Pharmacol Exp Ther 256:1010-1018.
28. Morishita S, Aoki S (2002). J Affect Disord 70:329-332.
29. Morishita et al. (1999). Psychiatry Clin Neurosci 53:11-15.
30. Mann et al. (1995). Br J Pharmacol 115:595-600.
31. Einat et al. (2003). J Neurosci 23: 7311-7316.
32. Shimizu et al. (1993). J Neurochem 60:595-601.
33. Cuellar-Quintero et al. (2001). Neuroreport 12:2195-2198.
34. Coppell et al. (2003). Neuropharmacology 44:903-910.
35. Saarelainen et al. (2003). J Neurosci 23:349-357.
36. Xu et al. (2003). NPP 28:53-62.

37. Wong et al. (1996). Biochem Biophys Res Commun 229:275-279.
38. Manev et al. (2001b). Eur J Pharmacol 420:R1-R2.
39. Santarelli et al. (2003). Science 301:805-809.
40. Malberg et al. (2000). J Neurosci 20:9104-9110.
41. Manev et al. (2001a). Eur J Pharmacol 411:67-70.
42. Dong J, Blier P (2001). Psychopharmacology (Berl) 155:52-57.
43. Lesch K P, Manji H K (1992). Biol Psychiatry 32:549-579.
44. Drigues et al. (2003). J Neural Transm 110:1413-1436.
45. Landgrebe et al. (2002). J Psychiatr Res 36:119-129.
46. Palotas et al. (2004). Int J Neuropsychopharmacol 7:401-413.
47. Coupland et al. (2005). Biol Psychiatry 57:1526-1534.
48. Barkai et al. (1978). Biol Psychiatry 13:65-72.
49. Einat et al. (2001). Behav Brain Res 118:77-83.
50. Einat et al. (1999). Psychopharmacology (Berl) 144:158-162.
51. Levine J (1997). Eur Neuropsychopharmacol 7:147-155.
52. Manji H K, Chen G (2000). Curr Psychiatry Rep 2:479-489.
53. Sarri et al. (1995). Journal of Pharmacology and Experimental Therapeutics 272:77-84.
54. Claro et al. (1993). J Neurochem 60:2078-2086.
55. Zhang et al. (2005). Neurosci Lett. 2005 Jul. 1-8; 382(1-2):134-8.
56. Watts et al. (1993). Eur J. Pharmacol. 242(2):165-72.
57. Undie A S, Friedman E (1990). J Pharmacol Exp Ther 253:987-992.
58. Undie A S (1999). Brain Res 816:286-294.
59. Panchalingam S, Undie A S (2001). Neuropharmacology 40:826-837.
60. Godfrey P P (1989). Biochem J 258:621-624.
61. Undie A S, Friedman E (1992). Eur J Pharmacol 226:297-302.
62. Stubbs E B, Jr. (1993). J Neurochem 60:1292-1299.
63. Billah M M, Michell R H (1978). Biochem Soc Trans 6:1033-1035.
64. Detke et al. (1995) Psychopharmacology (Berl) 121:66-72.
65. Porsolt et al. (1977) Arch Int Pharmacodyn Ther 229:327-336.
66. Porsolt et al. (1978) Eur J Pharmacol 47:379-391.
67. Golding E M, Vink R (1994) Brain Res 668:46-53.
68. Coderre T J (1992) Neurosci Lett 140181-184.
69. Yamada et al. (1994) Neurosci Lett 165:191-194.
70. Undie et al. (1994) J Neurochem 62:2045-2048.
71. Engleman et al. (1992) Neurochem Res 17:483-488.
72. Hingtgen et al. (1985) Biol Psychiatry 20:592-597.

Any publications mentioned in this specification are indicative of the levels of those skilled in the art to which the invention pertains. Further, these publications are incorporated by reference herein to the same extent as if each individual publication was specifically and individually incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of identifying a compound effective to treat or alleviate the symptoms of depression, comprising:
    contacting a tissue having a CDP-diacylglycerol and phosphoinositides metabolic activity with a potential antidepressant compound;
    determining a level of CDP-diacylglycerol and a level of inositol phosphate in the tissue after contact therewith; and
    comparing an index value that is a ratio of CDP-diacylglycerol to inositol phosphate in the tissue to a control index value, wherein a higher CDP-diacylglycerol/inositol phosphate index value in tissue treated with the compound indicates the potential compound has an antidepressant effect.

2. The method of claim 1, wherein the antidepressant is imipramine.

3. The method of claim 1, further comprising:
    treating a subject having a depressive disorder with the compound screened by the method.

4. A method of predicting therapeutic efficacy of an antidepressant drug regimen in a subject having a depressive disorder, comprising:
    administering a first selected drug regimen that is a combination of antidepressant drugs to the subject;
    determining a first CDP-diacylglycerol/inositol phosphate index value that is the ratio of a level of CDP-diacylglycerol to a level of inositol phosphate in the subject after administration;
    comparing the first index value to the CDP-diacylglycerol/inositol phosphate index values of subsequently and individually administered combinations of other selected antidepressants; wherein a higher relative index value correlates to therapeutic efficacy of the drug regimen.

5. The method of claim 4, wherein the combination of antidepressant drugs comprises a tricyclic antidepressant(s), a selective serotonin reuptake inhibitor(s) or an atypical antidepressant(s) or a synthetic antidepressant compound that increases production of CDP-diacylglycerol end synthesis of inositol phosphate in a depression-relevant brain tissue or blood platelets.

6. The method of claim 5, wherein the tricyclic antidepressant is desipramine or imipramine.

7. The method of claim 5, wherein the selective serotonin reuptake inhibitor is fluoxetine or paroxetine.

8. The method of claim 4, wherein the depressive disorder is major depression.

* * * * *